US007860669B2

(12) United States Patent
Najim Al-Khamis

(10) Patent No.: US 7,860,669 B2
(45) Date of Patent: Dec. 28, 2010

(54) SYSTEM, PROGRAM PRODUCT, AND RELATED METHODS FOR ESTIMATING AND MANAGING CRUDE GRAVITY IN FLOWLINES IN REAL-TIME

(75) Inventor: Mohammed Najim Al-Khamis, Qatif (SA)

(73) Assignee: Saudi Arabian Oil Company (SA)

( * ) Notice: Subject to any disclaimer, the term of this patent is extended or adjusted under 35 U.S.C. 154(b) by 318 days.

(21) Appl. No.: 12/140,844

(22) Filed: Jun. 17, 2008

(65) Prior Publication Data

US 2009/0312964 A1 Dec. 17, 2009

(51) Int. Cl.
*G01F 17/00* (2006.01)

(52) U.S. Cl. ........................................................ 702/50

(58) Field of Classification Search .................. 702/50, 702/137, 138; 137/10; 73/438; 438/32
See application file for complete search history.

(56) References Cited

U.S. PATENT DOCUMENTS 3,033,040 A 5/1962 Piros
3,175,403 A 3/1965 Nelson
3,483,732 A 12/1969 Gogarty
3,488,996 A 1/1970 Pfrehm
4,248,599 A * 2/1981 Mommessin et al. .......... 436/32
4,274,283 A 6/1981 Maus et al.
4,417,474 A * 11/1983 Elderton ...................... 73/438
4,757,709 A 7/1988 Czernichhow
5,182,940 A 2/1993 Bailey
6,550,327 B1 * 4/2003 Van Berk ..................... 73/438
6,633,043 B2 10/2003 Hegazi
6,687,643 B1 * 2/2004 Cason, Jr. ................... 702/137
6,734,963 B2 5/2004 Gamble
6,807,857 B2 * 10/2004 Storm et al. .................. 73/438
7,032,449 B2 4/2006 Rivas
7,668,688 B2 * 2/2010 Najim Al-Khamis ........ 702/138
2003/0226395 A1 12/2003 Storm et al.
2004/0139791 A1 7/2004 Johansen
2005/0034535 A1 2/2005 Sprague
2005/0182566 A1 8/2005 DiFoggio (Continued)

FOREIGN PATENT DOCUMENTS

CN 1338587 7/2001

(Continued)

OTHER PUBLICATIONS

The International Search Report and the Written Opinion for PCT/US2009/047606, Dated Jun. 17, 2009.

*Primary Examiner*—Tung S Lau
*Assistant Examiner*—Xiuquin Sun
(74) *Attorney, Agent, or Firm*—Bracewell & Giuliani LLP

(57) ABSTRACT

Systems, program product, and methods to estimate and manage flowing fluid characteristics of a fluid stream flowing through a pipeline in real-time, are provided. A system can include a vertically oriented extent of a pipeline for transporting crude oil, a pair of spaced vertically apart sensors or sensor assemblies connected to the vertically oriented extent to obtain pressure and temperature readings of the crude oil, a controller in communication with the pair of sensors or sensor assemblies, and crude oil analysis and management program product stored in the memory of the controller and adapted to determine or estimate density, specific gravity, and API gravity of the crude oil to thereby manage flowing fluid characteristics of the crude oil.

34 Claims, 8 Drawing Sheets

21 23 27 25 30 29 51 53 31 35 71 37 39 41 33 43
Computer
Memory
Program Product
User Interface
Graphical User Display
Input Device
Processor
Database

U.S. PATENT DOCUMENTS

2008/0257413 A1 * 10/2008 Noureldin et al. ............. 137/10

FOREIGN PATENT DOCUMENTS

| | | | |
|---|---|---|---|
| EP | 352203 | | 1/1990 |
| GB | 2041542 | A | 9/1980 |
| JP | 63132134 | | 4/1988 |
| WO | 9504869 | | 2/1995 |

* cited by examiner

SYSTEM, PROGRAM PRODUCT, AND RELATED METHODS FOR ESTIMATING AND MANAGING CRUDE GRAVITY IN FLOWLINES IN REAL-TIME

BACKGROUND OF THE INVENTION

1. Field of the Invention

The present invention relates generally to managing fluid characteristics of a fluid, and specifically to systems, apparatus, program product, and methods to estimate and manage flowing fluid characteristics of a fluid stream flowing through a pipeline.

2. Description of Related Art

Crude oil generally comprises a complex mixture of hydrocarbons of the various molecular weights plus other organic compounds of variable specific gravity and viscosity. Crude oil, however, also includes various impurities including gas, water, salt, etc. along with other chemicals compounds used in the extraction process. Accordingly, crude oil received from production wells is typically routed through a processing facility such as, for example, a gas oil separation plant (GOSP). Such gas oil separation plant can include, for example, a 2 or 3-stage oil-gas separation facility, with a 2 or 3-stage dehydrator/desalting train. A typical gas oil separation plant processes ~300 MBD of crude and ~100 MBD of water. The gas oil separation plants are generally designed to handle watercuts up to 30%, and some have been modified and retrofitted to handle higher watercuts. The crude oil exiting the gas oil separation plant is considered dehydrated dead crude oil.

Crude oil extracted from each separate oil well for processing at the gas oil separation plant, has generally been found to have its own unique characteristics. Responsively, in order to classify the oil coming from each separate oil well, the oil industry has developed various methodologies of grading the different types of crude oil. One of the most popular methodologies is the use of a grading system based on specific gravity/density developed by the American Petroleum Institute (API), a U.S trade association representing various companies involved in production, refinement, and distribution of oil and gas. According to such methodology, each volume of crude oil is assigned an API degree rating or grade which relates its specific gravity with that of water. According to the API scale, water is assigned a 10 degree API rating.

Crude oil is classified as light, medium, or heavy, according to its measured API gravity, with the lighter crude oil assigned a higher API gravity. In general, crude oil having a rating above approximately 31 API is considered in the industry to be "light," with oil having a rating (grade) above approximately 40 API considered to be "very light." Crude oil having an API gravity between approximately 22 and 31 API is considered in the industry to be "medium." Crude oil having an API gravity below approximately 22 is considered in the industry to be "heavy." Various other rating schemes are used to further define each specific volume of crude oil. For example, oil having a low sulphur content is identified as being "sweet," while crude oil having a high sulphur content is identified as being "sour."

The commercial value of a volume of crude oil generally depends upon its API gravity degree and on the needs of the buyer. Nevertheless, in general, crude oil having an API gravity of between 40 and 45 API tends to have the greatest commercial value. Accordingly, crude oil producers running multiple wells may wish to control production of the individual wells so that the overall deliverable volume of crude oil is maintained within a selected range of values or at least maintained above a minimum value.

Conventional practice to determine the API gravity, so far, has been to collect fluid samples and to send the samples to a laboratory for manual fluid density estimation. Because, in most of the cases, the crude grade for a certain field does not change much (i.e., production from the same reservoir/reservoirs may have almost similar crude grades), this manual method is generally considered quite practical. The Applicant has recognized, however, that for cases with a complex crude blend (i.e., mix of several produced crude grades) from several wells, for example, the manual method is not practical. In this case, a real time estimation of crude grade is required in order to ensure that the required produced crude grade is met at all times, and to facilitate adjusting the flow rates of certain wells with specific crude grades in order to maintain or to bring the overall produced crude grade back to the required or desired limit if outside such limit.

Other newly developed methodologies of determining API gravity, exist. For example, U.S. Pat. No. 6,633,043 by Hegazi et al., titled "Method for Characterization of Petroleum Oils Using Normalized Time-Resolved Fluorescence Spectra," describes a method based on time-resolved, laser-induced fluorescence spectroscopy for the characterization and fingerprinting of petroleum oils and other complex mixtures. The method depends on exciting the wavelength-resolved fluorescence spectra of manually obtained samples using ultraviolet pulsed laser radiation, measuring them at specific time gates within the temporal response of the excitation laser pulse, and comparing them in terms of their shapes, alone, without taking into account their relative intensities. U.S. Pat. No. 4,248,599 by Mommessin et al., titled "Process for Determining the API gravity of Oil by FID" describes determining the API gravity of a manually obtained oil sample by vaporizing its volatile and pyrolyzable components, measuring the ratio of the amount vaporized within a range of relatively high temperatures to the total amount vaporized. Again, the inventor has recognized that for cases with a complex crude blend (i.e., mix of several produced crude grades), such manual methodologies are not practical.

Although not understood by the inventor as being recognized in industry as an acceptable method for obtaining an API gravity of a complex blend of crude oil, the inventor recognizes that various methodologies of determining density of a fluid, nevertheless, exists. For example, U.S. Pat. No. 6,807,857, by Storm Jr. et al., titled "Method and Apparatus for Determining Density of a Flowing Fluid" describes a tool and process for measuring the density of a flowing fluid using two sets of measurement readings each taken from a corresponding pair of pressure assessment zones of a half-loop configured fluid conducting tool. WO 95/04869 by Kyllingstad, titled "A Method and an Apparatus for Measuring Density and Pressure Drop in a Flowing Fluid" similarly describes a pipe loop for receiving fluid from a main flow and having two branches each including a pair of spaced apart pressure sensors which provide data to calculate the liquids density and pressure loss per length unit. CN 13385, by Wang, titled "In-Line Continuous Measuring Method for Concentration and Density of Liquid Medium" describes a method and apparatus for measuring density which includes a vertical measuring tube for receiving an upward vertical flow and having two pressure measuring points, a differential pressure transducer used to measure their differential pressure, a medium temperature transducer positioned in the two pressure measuring points, and an ambient temperature transducer. U.S. Pat. No. 7,032,449 by Rivas, titled "Measurement of Fluid Properties in Vessel and Sensor for Same" describes a sensor for measuring properties of a fluid in a vessel having sensors spaced vertically along the sensor body inserted into a container. U.S. Pat. No. 6,687,643 by Cason Jr., titled "In-situ Sensor System and Method for Data Acquisition in Liquids" describes a system and method which measures the density of a static liquid in a container using pressure sensors positioned at two separate locations and separated by a fixed distance, and a temperature sensor. U.S. Pat. No. 3,033,040 by Piros, titled "Density Measuring Apparatus" describes a density meter for measuring the density of liquids, and controlling the proportion of constituent liquids present in blends so that the blend has a given density. The density meter determines density of fluid mixture extracted by a pump from a main flow using a pressure difference between a pressure maintaining (constant pressure) device positioned at an upper end of a vertical conduit and a pressure measuring device located at its lower end. U.S. Pat. No. 3,483,732 by Gogarty, titled "Continuous Density-Determining Device and Process" describes an apparatus which includes a conduit for extracting fluid to determine its density, a means for rendering a flowing liquid turbulent, a liquid flow measuring device, and a differential pressure transducer to determine a difference in pressure between two pressure points along the conduit.

Each of these devices, however, fails to provide a process for measuring the density of flowing fluid in a main flow line in real-time, and/or requires either an extraction pump, a separate sampling line to extract fluid from the main flow, a means to pump fluid upwardly through a vertical component, a collection or discharge line disruptively inserted into the main flow stream, or a combination thereof. Nor does either of these devices provide necessary means for estimating, and thus controlling, API gravity. Recognized by the inventor, therefore, is the need for a process setup that enables real-time estimation of fluid density and crude API gravity of a liquid fluid stream flowing through a pipeline in a processing facility, which does not require the addition of an external sampling line, the addition of a sampling or extraction pump, or application of a fluid collector, which would tend to impede or disrupt a fluid flow.

SUMMARY OF THE INVENTION

In view of the foregoing, embodiments of the present invention advantageously provide a system, apparatus, program product, and methods for estimating and managing flowing fluid characteristics of a fluid stream, in real time, which does not require the addition of an external sampling line, the addition of a sampling or extraction pump, application of a fluid collector, or use of manual sampling techniques. Embodiments of the present invention also advantageously provide a system, apparatus, program product, and methods to estimate and manage flowing fluid characteristics of a fluid stream of, for example, dehydrated degassed dead crude oil flowing through a pipeline in a processing facility. Embodiments of the present invention advantageously overcome the inadequacies of conventional density measuring equipment through use of a pair of dual pressure-temperature transducers inserted into a pair of vertically spaced apart pressure taps positioned through a vertically oriented (i.e., not substantially horizontal) section of main flow pipeline carrying a downward flowing flow stream of the crude oil processed by the processing facility.

Embodiments of the present invention provide a system to estimate and manage flowing fluid characteristics of a fluid stream flowing through a pipeline in a processing facility, in real-time. According to an embodiment of the system, the system can include at least a portion of a pipeline for transporting fluid. The fluid can include, for example, dehydrated degassed crude oil received from a plurality of wells and processed by a processing facility. The at least a portion of the pipeline can include a vertically oriented extent substantially vertically oriented so that the crude oil flowing through the vertically oriented extent flows downward between a first location and a second location along the vertically oriented extent, vertically spaced apart from and vertically below the first location. The system can also include at least one first sensor connected to the at least a portion of the pipeline at the first location to provide at least one signal indicative of pressure and temperature of the crude oil at the first location, at least one second sensor connected to the at least a portion of the pipeline at the second location to provide at least one signal indicative of pressure and temperature of the crude oil at the second location, and a controller including a processor in communication with the at least one first sensor and the at least one second sensor and adapted to estimate and manage flowing fluid characteristics of the crude oil. The system can also include crude oil analysis and management program product stored in the memory of the controller. The system can further include a plurality of flow control valves each in communication with the controller either directly or through an engineering station. Each flow control valve is separately positioned to individually control a flow rate of crude oil entering the processing facility, and thus, is positioned to collectively control a flow rate of crude oil entering the at least a portion of the pipeline. As such, according to an embodiment of the system, the crude oil can provide a complex crude blend including a plurality of crude grades provided by the plurality of oil wells.

According to an embodiment of the system, the crude oil analysis and management program product can include instructions that when executed by the processor of the controller, cause the controller to perform the operations of determining fluid pressure and temperature of the crude oil at the first location responsive to the at least one signal provided by the at least one first sensor, determining fluid pressure and temperature of the crude oil at the second location responsive to the at least one signal provided by the at least one second sensor, and estimating density of the crude oil flowing through the vertically oriented extent of the at least a portion of the pipeline responsive to: the determined fluid pressure at the first location, the determined fluid pressure at the second location, the vertical elevation between a pressure sensor portion of the at least one first sensor and a pressure sensing portion of the at least one second sensor, and approximate flow rate of the crude oil flowing downward through the vertically oriented extent of the at least a portion of the pipeline. The operations can also include estimating specific gravity of the crude oil flowing through the vertically oriented extent of the at least a portion of the pipeline at standard condition responsive to: the estimated density of the crude oil, determined fluid temperature at the first location, and the determined fluid temperature at the second location; and estimating API gravity of the crude oil flowing through the vertically oriented extent of the at least a portion of the pipeline at standard condition responsive to the estimated specific gravity of the crude oil flowing through the vertically oriented extent of the pipeline. The operations can further include comparing the estimated API gravity of the crude oil flowing through the vertically oriented extent of the at least a portion of the pipeline to at least one threshold value to determine if the API gravity has failed to meet the at least one threshold value to thereby maintain the API gravity above a preselected desired minimum value or within a preselected desired range limit, and adjusting the flow rate of one or more of the plurality of wells responsive to determining that the API gravity fails to meet the at least one threshold value.

Embodiments of the present invention also include crude oil analysis and management program product stored in a tangible computer medium to estimate and manage flowing fluid characteristics of a fluid stream flowing through a pipeline in real-time. According to an embodiment of the program product, the program product can include instructions that when executed by a computer, cause the computer to perform the operations of determining fluid pressure of crude oil at along a vertically oriented extent of a pipeline carrying crude oil flowing downward between the first location and a second location substantially spaced apart from the first location along the vertically oriented extent and vertically below the first location responsive to at least one signal provided by at least one first sensor associated with the first location, and determining fluid pressure of the crude oil at the second location responsive to at least one signal provided by at least one second sensor associated with the second location. The operations can also include estimating API gravity of the crude oil flowing through the vertically oriented extent of the pipeline responsive to: the determined fluid pressure at the first location, the determined fluid pressure at the second location, vertical elevation between the at least one first sensor and the at least one second sensor, and approximate flow rate of the crude oil flowing through the vertically oriented extent of the pipeline. The operation of estimating API gravity can include the operations of estimating density of the crude oil flowing through the vertically oriented extent of the pipeline, determining fluid temperature of the crude oil at the first location responsive to the at least one signal provided by the at least one first sensor, determining fluid temperature of the crude oil at the second location responsive to the at least one signal provided by the at least one second sensor, and estimating specific gravity of the crude oil flowing through the vertically oriented extent of the pipeline at standard condition responsive to: the estimated density of the crude oil, determined fluid temperature at the first location, and the determined fluid temperature at the second location, to thereby estimate the API gravity of the crude oil at standard at standard conditions.

The operations can further include comparing the estimated API gravity of the crude oil flowing through the vertically oriented extent of the pipeline to at least one threshold value to determine if the API gravity has failed to meet the at least one threshold value to thereby maintain the API gravity above a preselected desired minimum value or within a preselected desired range limit; and providing an adjustment signal to adjust a flow rate of one or more of a plurality of wells each having at least one flow control valve each separately positioned to control a flow rate of crude oil entering the pipeline (e.g., via a processing facility) received from a corresponding separate one of the plurality of oil wells.

Embodiments of the present invention also include methods for estimating and managing flowing fluid characteristics of a fluid stream flowing through a pipeline (e.g., in a processing facility), in real-time. According to an embodiment of a method, the method can include the steps of determining fluid pressure and temperature of a flowing fluid (e.g., dehydrated degassed crude oil) at a first location along a vertically oriented extent of a pipeline carrying the dehydrated degassed crude oil flowing downward between the first location and a second location substantially vertically spaced apart from the first location along the vertically oriented extent and vertically below the first location, and determining fluid pressure and temperature of the dehydrated degassed crude oil at the second location along the vertically oriented extent of the pipeline. The fluid pressure at the first location can be determined using a non-obstructive first pressure transducer coupled to a first fluid pressure tap. Similarly, the fluid pressure at the second location can be determined using a non-obstructive second pressure transducer coupled to a second fluid pressure tap and positioned at a predetermined (preselected) vertical elevation below that of the first pressure transducer.

The steps can also include estimating specific gravity of the crude oil flowing through the vertically oriented extent of the pipeline responsive to: the determined fluid pressure at the first location, the determined fluid pressure at the second location, the vertical elevation between the first location and the second location, and approximate flow rate of the crude oil flowing through the vertically oriented extent of the pipeline; and estimating API gravity of the crude oil flowing through the vertically oriented extent of the pipeline at standard condition responsive to: the estimated specific gravity of the crude oil flowing through the vertically oriented extent of the pipeline, the determined fluid temperature at the first location, and the determined fluid temperature at the second location. The steps can further include determining a dynamic condition correction factor responsive to the predetermined flow rate value to thereby account for frictional pressure loss between the first and the second locations, and determining or otherwise estimating a density of the crude oil flowing through the vertically oriented extent of the pipeline.

The steps can also include comparing the estimated API gravity of the crude oil flowing through the vertically oriented extent of the pipeline to at least one threshold value to determine if the API gravity has failed to meet the at least one threshold value, and adjusting a flow rate of one or more of a plurality of wells supplying the pipeline either directly or through a processing facility responsive to determining that the API gravity fails to meet the at least one threshold value to thereby maintain the API gravity above a preselected desired minimum value or within a preselected desired range limit.

According to another embodiment of a method for estimating and managing flowing fluid characteristics of a fluid stream flowing through a pipeline in real-time, the method can include the steps of determining fluid pressure of crude oil at a first location along a vertically oriented extent of a pipeline carrying the crude oil flowing downward between the first location and a second location substantially spaced apart from the first location along the vertically oriented extent and vertically below the first location, and determining fluid pressure at the second location along the vertically oriented extent of the pipeline. The fluid pressure can be determined using a first pressure sensor extending through a first portion of an outer wall surface of the pipeline, the fluid pressure at the second location can be determined using a second pressure sensor extending through a second portion of the outer wall surface of the pipeline, and the first and second portions of the outer wall surface of the pipeline can have a predetermined vertical elevation therebetween.

The method can also include the steps of determining a dynamic condition correction factor responsive to a predetermined flow rate value of the crude oil flowing through the pipeline and responsive to a calibration factor lookup table or a result of an empirical flow correlation to thereby account for frictional pressure loss between the first and the second locations when estimating density, and estimating density of the crude oil flowing through the vertically oriented extent of the pipeline responsive to: the determined fluid pressure at the first location, the determined fluid pressure at the second location, the vertical elevation between the first location and the second location, and approximate flow rate of the crude oil flowing through the vertically oriented extent of the pipeline (e.g., via the dynamic condition correction factor).

The method can also include determining fluid temperature at the first location along the vertically oriented extent of the pipeline, determining fluid temperature at the second location along the vertically oriented extent of the pipeline, estimating specific gravity of the crude oil flowing through the vertically oriented extent of the pipeline at standard condition responsive to the estimated density, determined fluid temperature at the first location, and the determined fluid temperature at the second location, and estimating API gravity of the crude oil flowing through the vertically oriented extent of the pipeline at standard condition responsive to the estimated specific gravity of the crude oil flowing through the vertically oriented extent of the pipeline.

The method can further include comparing the estimated API gravity of the crude oil flowing through the vertically oriented extent of the pipeline to at least one threshold value to determine if the API gravity has failed to meet (or has exceeded) the at least one threshold value, and adjusting a flow rate of one or more of the plurality of wells responsive to determining that the API gravity fails to meet (or exceeds) the at least one threshold value to thereby maintain the API gravity above a preselected desired minimum value or within a preselected desired range limit.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

DETAILED DESCRIPTION

The present invention will now be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout.

FIGS. 1-11 illustrate a system, apparatus, program product, and methods for estimating and managing flowing fluid characteristics of a fluid stream flowing through a pipeline in a processing facility in real-time. As will be described or detailed below, various embodiments of the present invention can provide a system, apparatus, program product, and methods which do not require the addition of an external sampling line, the addition of a sampling or extraction pump, or application of a fluid collector. Various embodiments of the present invention also provide a system, apparatus, program product, and methods to estimate and manage flowing fluid characteristics of a fluid stream of fluid in the form of dehydrated degassed dead crude oil flowing through a pipeline in a processing facility. Various embodiments of the present invention beneficially overcome the inadequacies of conventional density measuring equipment through use of a pair of dual pressure-temperature transducers inserted into a pair of vertically spaced apart pressure taps positioned through a vertically oriented (i.e., not substantially horizontal) section of main flow pipeline carrying crude oil processed by the processing facility.

Figure 1:
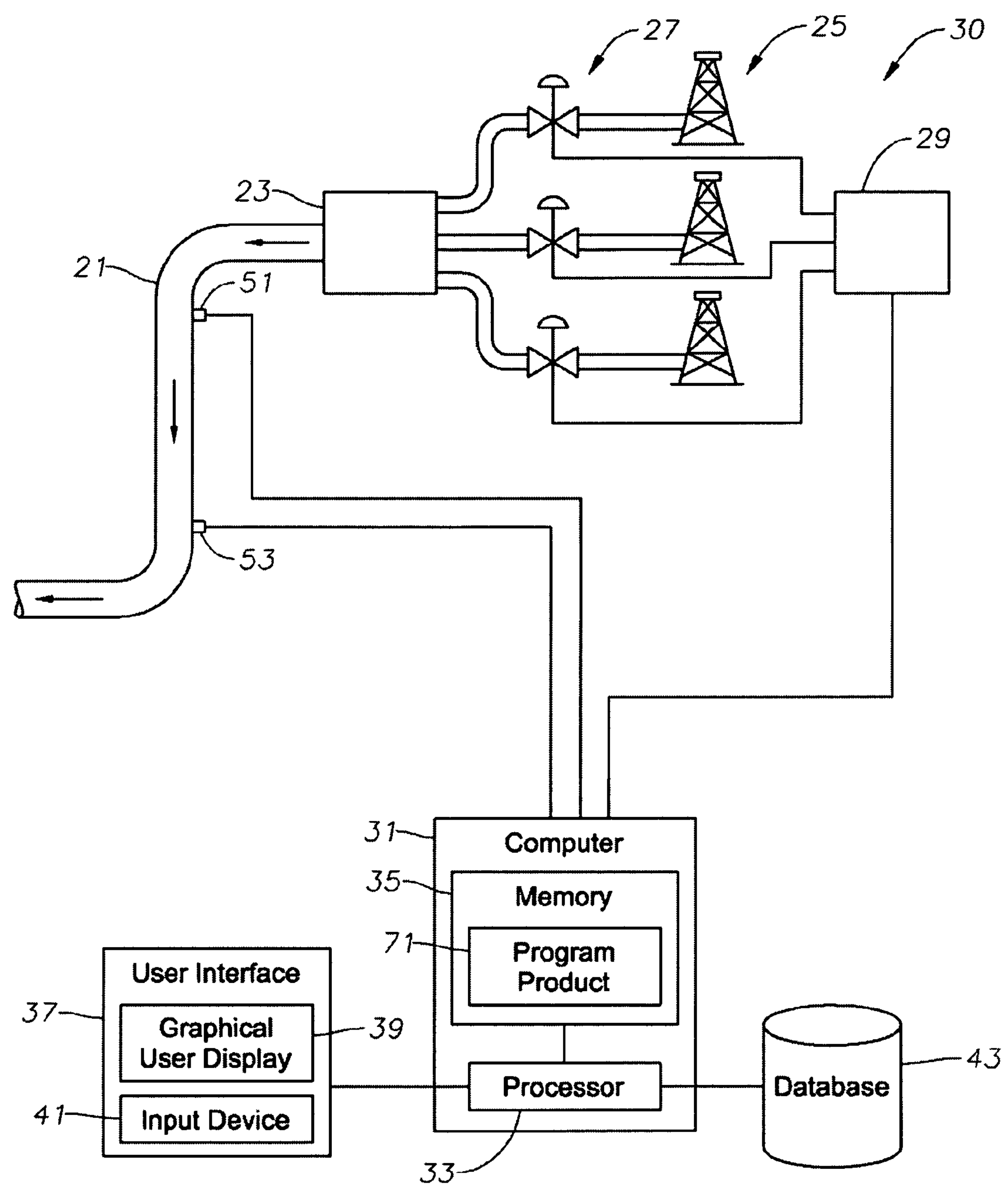
FIG. 1 is a schematic block diagram of a system to estimate and manage flowing fluid characteristics of fluid flowing through a pipeline according to an embodiment of the present invention.
Figure 2:
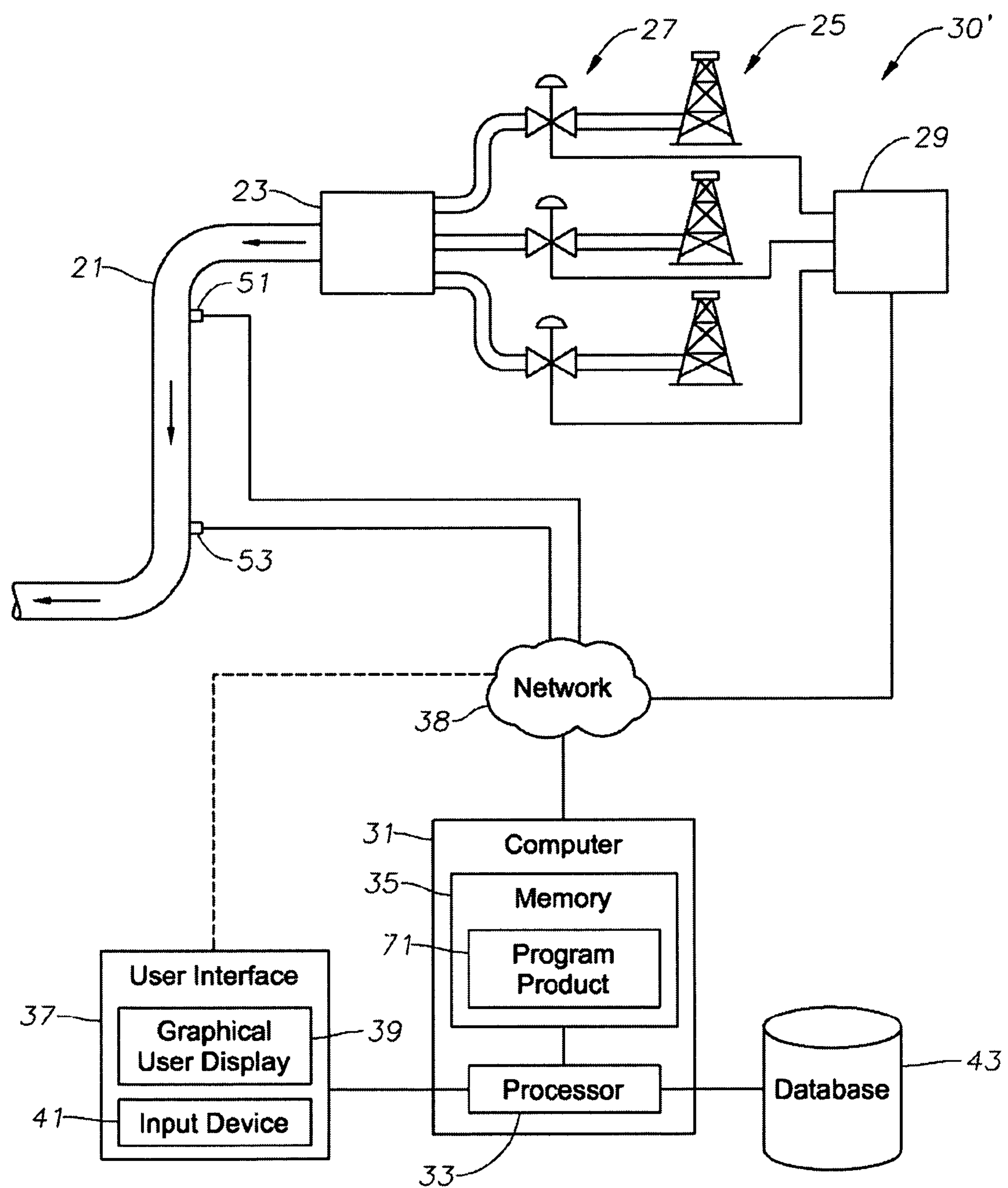
FIG. 2 is a schematic block diagram of a system to estimate and manage flowing fluid characteristics of fluid flowing through a pipeline according to an embodiment of the present invention.

More specifically, as perhaps best shown in FIGS. 1-2, embodiments of the present invention can include a system 30, 30', to estimate and manage flowing fluid characteristics of a fluid stream of fluid in the form of dehydrated degassed dead crude oil flowing through a pipeline 21 in or emanating from a processing facility 23 for transporting dehydrated degassed dead crude oil to a destination facility (not shown). The processing facility 23 receives wet gasified crude oil from and is in fluid communication with, a plurality of oil wells 25, each having a flow control device or valve 27 associated therewith and controlled by an engineering station 29. As will be described in more detail below, in the illustrated configuration, the flow control valves 27 are each in communication with a system computer or controller 31, manually or through automated systems via the engineering station 29, to control a flow rate of crude oil entering the processing facility 23, and thus, to control the flow rate and/or blend of the processed crude oil entering (and therefore exiting) the pipeline 21.

The wells 25 can have varying grades of crude oil resulting in the process crude oil processed by processing facility 23 having a complex crude blend. Particularly, although wells 25 from the same area tend to have similar grades, one or more of the wells 25 can have either an exceptionally high grade or an exceptionally low grade. Further, although all of the wells 25 may be producing a somewhat similar grade, one or more may be below a minimum threshold which, if not restricted, would result in the overall complex blend falling below some minimum threshold value.

As noted above, the system 30, 30', can include a fluid characteristics analysis and management controller or other form of computer 31. Such computer 31 can contain or otherwise include a processor 33, and memory 35 coupled to the processor 33 to store software and database records therein, for example, connected directly to system/non-system components (see, e.g., FIG. 1) and/or networked to such components (see, e.g., FIG. 2). Note, the computer 31 can be in the form of a personal computer or in the form of a server serving multiple user interfaces 37.

The system 30, 30', can also include a user interface 37 which can include a graphical display 39 for displaying graphical images, and a user input device 41 as known to those skilled in the art, to provide a user access to manipulate the software and database records. Accordingly, the user interface 37 can be either directly connected to the computer 31 or through a network 38, as known to those skilled in the art.

The system 30, 30', can further include a database 43 stored in the memory 35 (internal or external, networked, or non-networked) of the fluid characteristics analyzing computer 31 and having a various standard condition values, flow rate values, and other parameters, discussed below, utilized in analyzing and recording the fluid characteristics of the fluid flowing through pipeline 21, described in more detail below.

Figure 3:
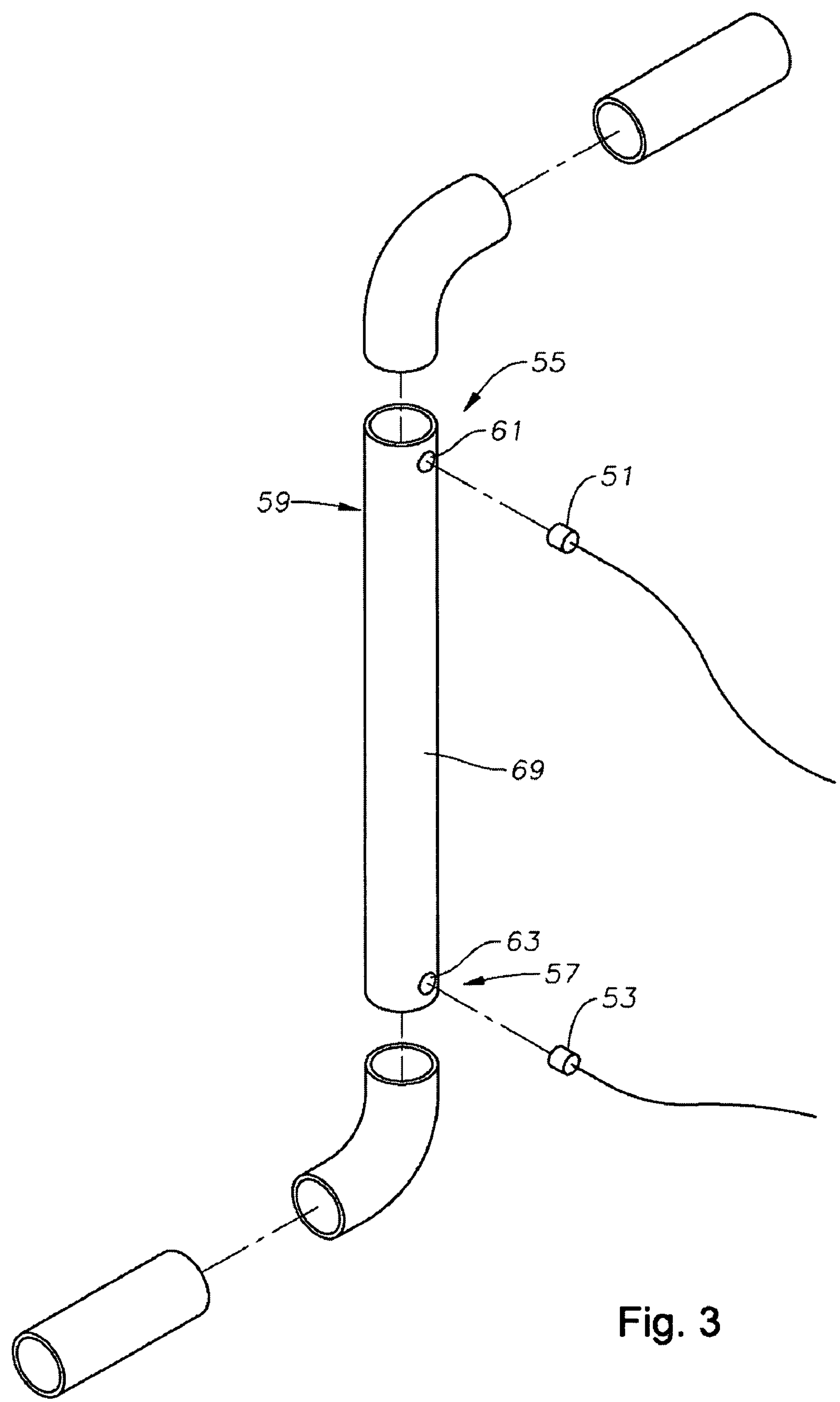
FIG. 3 is an exploded perspective view of a portion of a pipeline including a pressure and temperature sensor assembly according to an embodiment of the present invention.
Figure 4:
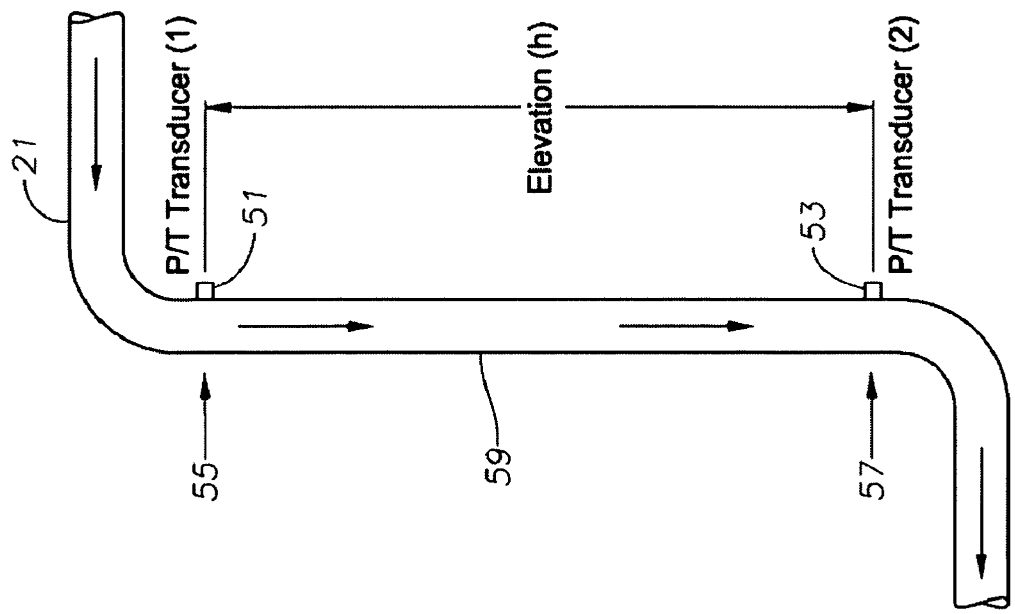
FIG. 4 is a schematic diagram of a portion of a pipeline including a pressure and temperature sensor assembly according to an embodiment of the present invention.

As perhaps best shown in FIGS. 3-4, the system 30, 30', can also include a pair of sensors/sensor assemblies 51, 53 connected along or to separate, spaced apart, portions or locations 55, 57, of a vertically oriented extent 59 of the pipeline 21 vertically oriented to some azimuth greater than zero degrees, but preferably at least approximately 45 degrees, and more preferably approximately 90 degrees, so that the crude oil flowing through the vertically oriented extent flows downward between the first location 55 and the second location 57 along the vertically oriented extent 59. As perhaps best shown in FIG. 4, in the exemplary configuration, the second location 57 can be substantially vertically spaced apart from and vertically below the first location 55, at a preselected elevation "h." The first sensor/sensor assembly 51 is positioned at the first location 55 to provide at least one signal indicative of pressure of the crude oil at the first location 55. The second sensor/sensor assembly 53 is positioned at the second location 57 to provide at least one signal indicative of pressure of the crude oil at the second location 57. Note, the elevation "h" between sensors/sensor assemblies 51, 53, can vary depending upon the desired accuracy, but should generally be greater than approximately 10 feet, to overcome accuracy limitations of the pressure sensors/sensor assemblies 51, 53. Notably, the larger the elevation "h," the better the accuracy due to the provision of a larger sample. Nevertheless, due to wireline/wireless connectivity requirements, the elevation "h" is preferably between 20 feet and 100 feet, and more preferably between 25 feet and 35 feet. Note also, in configurations where the vertically oriented extent 59 of the pipeline 21 is not oriented normal to the earth's surface, the elevation "h" will not be the physical distance between respective locations 55, 57, where pressure readings are being taken, but rather the distance between two parallel planes each separately passing through a respective location 55, 57, where the respective pressure readings are being taken, and each perpendicular to the force of gravity.

According to a preferred configuration, the first sensor/sensor assembly 51 also provides the temperature of the crude oil at the first location 55. Similarly, the second sensor/sensor assembly 53 is positioned at the second location 57 to provide at least one signal indicative of pressure of the crude oil at the second location 57. According to a preferred configuration, the second sensor/sensor assembly 53 also provides the temperature of the crude oil at the second location 57. Particularly, sensor/sensor assemblies 51, 53, can each be a combined pressure-temperature transducer as known to those skilled in the art, each typically requiring only a single aperture 61, 63, extending through the outer surface 69 of the vertically oriented extent 59 of the pipeline 21 at their respective locations 55, 57. Note, however, the use of separate temperature transducers is within the scope of the present invention.

Further, according to various embodiments of the present invention, the spacing of the temperature transducers between each other at their respective locations 55, 57, need not be exact or substantially exact, although precision dictates preferably determining the respective first and second temperatures at the respective first and second locations 55, 57, at a same axial position as that of the first and the second pressure readings, respectively. That is, the temperatures should be taken at as close as possible to where the pressures are taken, or at least as close as possible to a same axial location along the vertically oriented extent 59 of the pipeline 21 as that of the first and the second pressures if separate temperature/pressure transducers or other sensors 51, 53, are utilized at the respective first and second locations 55, 57.

Still further, as shown in FIG. 3, at least portions of the first sensor/sensor assembly 51 can extend through a first pressure tap 61 in an outer wall surface 69 of the vertically oriented extent 59 of the pipeline 21 at the first location 55. Similarly, at least portions of the second sensor/sensor assembly 53 can extend through a second pressure tap 63 in the outer wall surface 69 of the vertically oriented extent 59 of the pipeline 21 at the second location 57. According to an embodiment of the system 30, 30', the crude oil flowing downward through the sample area of the vertically oriented extent 59 of the pipeline 21 is in fluid contact with at least portions of the first and the second pressure sensors/sensor assemblies 51, 53. Still further, according to an embodiment of the system 30, 30', the sensors/sensor assemblies 51, 53, can extend through the outer wall surface 69 at the respective locations 55, 57, to the minimum extent necessary to sufficiently obtain the desired pressure and/or temperature readings, and still minimize any fluid flow disruption.

The sensors/sensor assemblies 51, 53, according to such embodiment of the system 30, 30', can also be strategically positioned, for example, through taps 61, 63, as perhaps best shown in FIG. 3, to thereby negate a need for a fluid collection extension to be separately inserted into the flow stream of the pipeline 21, to gather or otherwise interface the flowing fluid (e.g., crude oil) flowing within the pipeline 21 with the sensors/sensor assemblies 51, 53, to thereby perform the pressure and/or temperature analysis on the flowing fluid. Further, the sensors/sensor assemblies 51, 53, according to an embodiment of the system 30, 30', can also be strategically positioned along a vertically oriented extent (e.g., extent 59), as perhaps best shown in FIGS. 3-4, to thereby negate a need for a separate fluid sampling line to obtain a sample of the flowing fluid flowing through pipeline 21, to thereby perform such pressure and/or temperature analysis on the fluid within the pipeline 21.

Still further, the sensors/sensor assemblies 51, 53, according to an embodiment of the system 30, 30', can also be strategically positioned along a vertically oriented extent (e.g., extent 59) at separate elevations (e.g., separated by elevation h), as perhaps best shown in FIGS. 3-4, to thereby negate a need for a fluid sampling pump (not shown) to extract the fluid within the pipeline 21 for pressure and/or temperature analysis. That is, rather than requiring utilization of a fluid sampling pump, such embodiment of the system 30, 30', beneficially utilizes gravity to establish a pressure differential between sensors/sensor assemblies 51, 53, reducing the complication of mechanical components needed to interface with the pipeline 21 and the amount and cost of components needed to perform an initial installation or a retrofit of an existing pipeline 21. Beneficially, for a retrofit, managers need only select a vertically oriented portion of the pipeline 21 for inclusion of taps 61, 63, either pre-pipeline deployment or post-pipeline deployment, if such taps 61, 63, do not already exist.

The system 30, 30', can include crude oil analysis and management program product 71 stored in memory 35 of the fluid characteristics analysis and management computer 31. The program product 71, according to an embodiment of the system 30, 30', is adapted: to receive pressure and/or temperature inputs, to provide estimates of various flowing fluid characteristics including, for example, one or more of the following: an estimated density of the flowing fluid (e.g., crude oil) flowing through the pipeline 21, an estimated specific gravity of the flowing fluid, and an estimated API gravity of the flowing fluid, etc. Note, the crude oil analysis and management program product 71 can be in the form of microcode, programs, routines, and symbolic languages that provide a specific set for sets of ordered operations that control the functioning of the hardware and direct its operation, as known and understood by those skilled in the art. Note also, the crude oil analysis and management program product 71, according to an embodiment of the present invention, need not reside in its entirety in volatile memory, but can be selectively loaded, as necessary, according to various methodologies as known and understood by those skilled in the art of computer systems.

Figure 6:
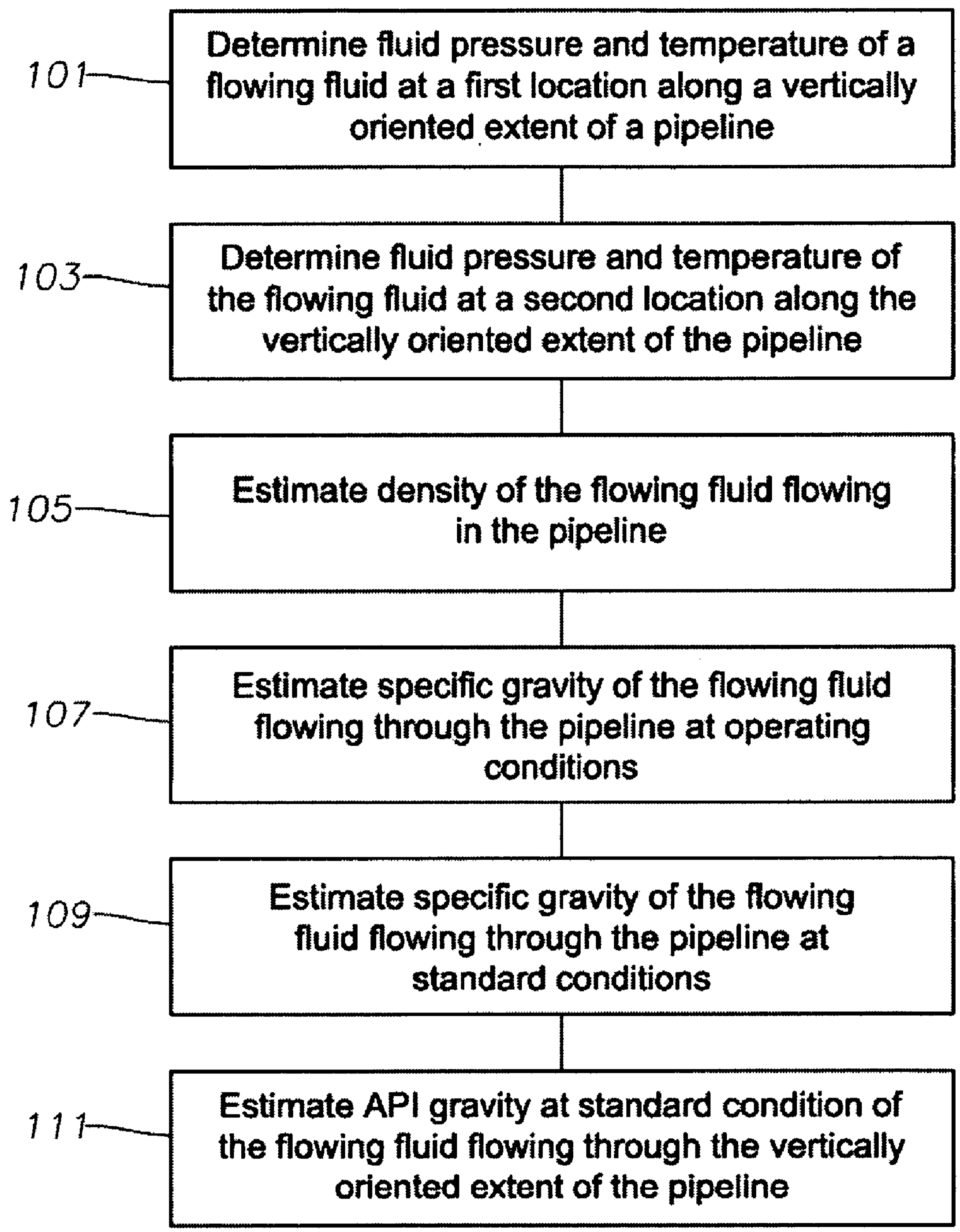
FIG. 6 is a schematic flow diagram of a method and operations for estimating and managing flowing fluid characteristics of a fluid flowing through a pipeline according to an embodiment of the present invention.

FIG. 6 provides a high-level flow diagram illustrating a method (and operations) for estimating and managing flowing fluid characteristics of a fluid stream (e.g., dehydrated and/or degassed crude oil) flowing through a pipeline (e.g., pipeline 21), for example, in a processing facility (e.g., process facility 23) in real-time, at operating and standard conditions. According to the illustrated embodiment of the present invention, the method can include the steps of determining fluid pressure and temperature of the crude oil at a first location 55 (e.g., proximal or upper end portion along a vertically oriented extent 59) of the pipeline 21 carrying the crude oil flowing downward between the first location 55 and a second location 57 (e.g., distal or lower end portion along a vertically oriented extent 59) substantially vertically spaced apart from the first location 55 along the vertically oriented extent 59 and vertically below the first location 55 (block 101), and determining fluid pressure and temperature of the crude oil at the second location 57 along the vertically oriented extent 59 of the pipeline 21 (block 103). According to an exemplary configuration illustrated in FIG. 3, the fluid pressure and temperature at the first location 55 can be determined using a first transducer 51 coupled to a first fluid tap 61 either pre installed or retrofitted through an outer surface 69 of the vertically oriented extent 59. The fluid pressure and temperature at the second location 57 can be determined using a second transducer 53 coupled to a second fluid tap 63. The first and the second pressure and/or temperature taps 61, 63, can be installed such that when the vertically oriented extent 59 of the pipeline 21 is operationally inserted or otherwise installed, the taps 61, 63, have a predetermined or otherwise preselected vertical elevation therebetween, shown as elevation "h" in FIG. 4. Note, according to a preferred installation arrangement, when operatively installed, the first and the second transducers (or other sensors) 51, 53, are extended into or through the taps 61, 63, sufficiently to obtain a robust reading, but without substantially impeding fluid flow of the crude oil in the pipeline 21, or causing a substantial amount of turbulence due to an impacted surface area of the sensors 51, 53, when impacted or otherwise in free contact with the flowing fluid.

The method can also include the step of estimating API gravity at standard condition of the crude oil flowing through the vertically oriented extent 59 of the pipeline 21 (block 111), for example, either directly responsive to: the determined fluid pressure and temperature at the first location 55, the determined fluid pressure and temperature at the second location 57, vertical elevation "h" between the sensors 51, 53, and approximate flow rate of the crude oil flowing through the vertically oriented extent 59 of the pipeline 21; or indirectly by first solving for: the density (block 105), specific gravity at operating conditions (block 107), and/or specific gravity at standard conditions (block 109) of the crude oil flowing through the vertically oriented extent 59 of the pipeline 21.

According to an embodiment of the method, the API gravity at standard condition can be estimated using the following calculations:

$$\rho_c = \frac{P_2 - P_1}{h} + CF;$$

$$\gamma = \frac{\rho_c}{\rho_w};$$

$$\text{Crude } API = \left(\frac{141.5}{\gamma} - 131.5\right);$$

$$\gamma_{STD} = \gamma\left[1 - \beta\left(60^\circ F - \left(\frac{T_1 + T_2}{2}\right)\right)\right];$$

$$\text{Crude } API_{STD} = \left(\frac{141.5}{\gamma_{STD}} - 131.5\right);$$

where:

$\rho_c$ is the density of the crude oil, $P_1$ is the determined fluid pressure at the first location, $P_2$ is the determined fluid pressure at the second location, h is the vertical elevation between the first and the second fluid pressure taps/sensors in the vertically oriented extent of the pipeline, CF is a correction factor that accounts for frictional pressure loss between the first and the second locations, $\gamma$ is the specific gravity of the crude oil at operating condition, $\rho_w$ is the density of water: 62.4 lb/ft$^3$, API is the API at current operating conditions, $\gamma_{STD}$ is the specific gravity of the crude oil at standard condition, $\beta$ is the coefficient of isobaric thermal expansion, $T_1$ is the determined fluid temperature at the first location, $T_2$ is the determined fluid temperature at the second location, and $API_{STD}$ is the API at current standard conditions.

Notably, when implemented in association with the processing facility 23, the flow rate of the fluid in pipeline 21 is known, or at least, readily predetermined. Accordingly, according to an embodiment of the method, the flow rate of the crude oil through the vertically oriented extent 59 of the pipeline 21 can be based on a value of the flow rate entering the pipeline 21 at the processing facility 23. Accordingly, the method can also include the step of determining the correction factor "CF" made responsive to (e.g., based upon) the predetermined flow rate/value and responsive to a calibration factor lookup table (not shown) stored, for example, in database 43, to thereby account for frictional pressure loss between the first and the second locations 55, 57. According to another embodiment of the method, the step of determining the correction factor "CF" is made responsive to the predetermined flow rate value and responsive to a result of an empirical flow correlation to thereby account for the frictional pressure loss between the first and the second locations 55, 57. As known and understood by those skilled in the art the empirical flow correlation can provide an equation fit of the correction factor table.

Figure 7:
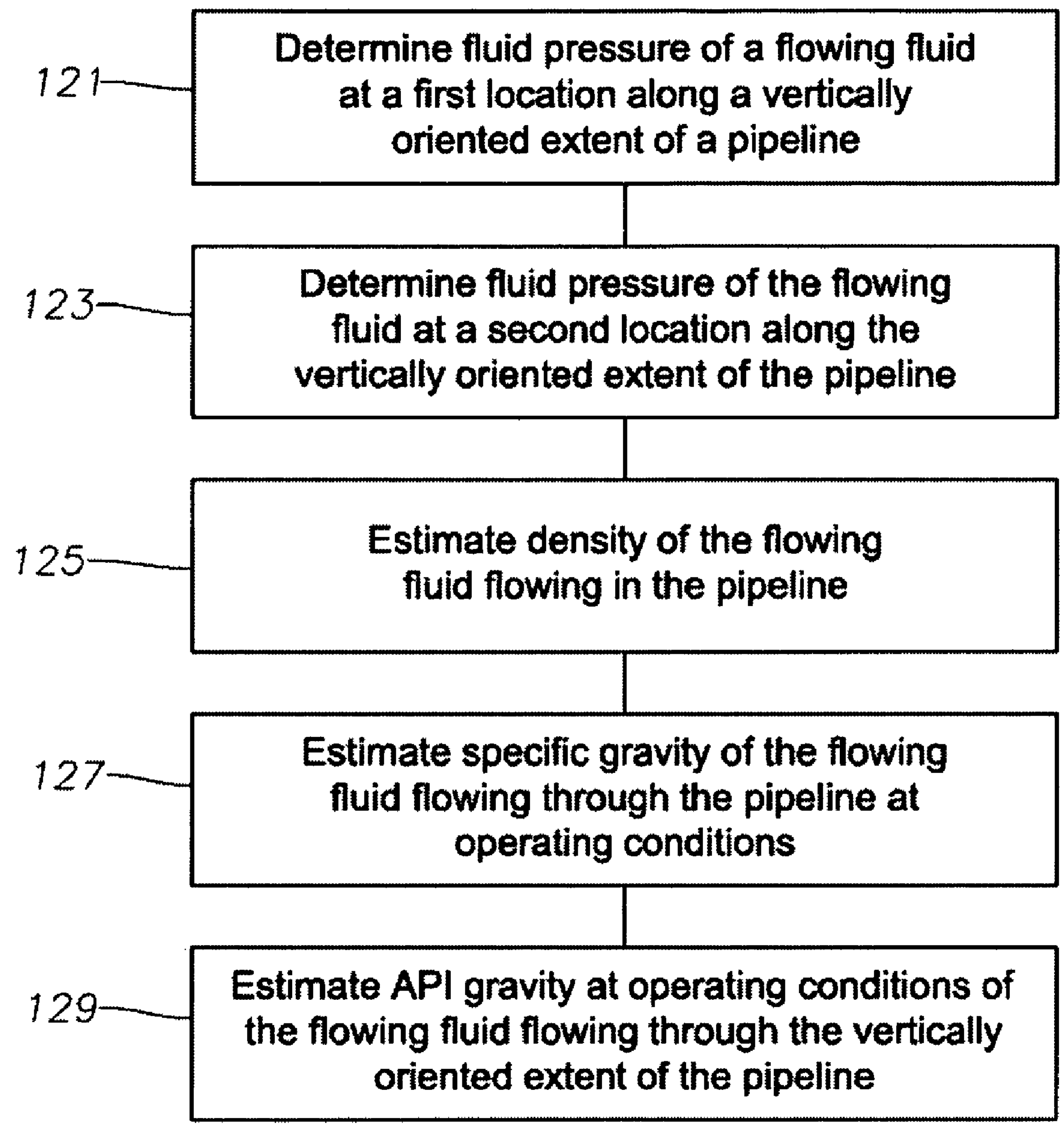
FIG. 7 is a schematic flow diagram of a method and operations for estimating and managing flowing fluid characteristics of a fluid flowing through a pipeline according to an embodiment of the present invention.

FIG. 7 provides a high-level flow diagram illustrating a method for estimating and managing flowing fluid characteristics of a fluid stream (e.g., dehydrated and/or degassed crude oil) flowing through a pipeline (e.g., pipeline 21), for example, in a processing facility (e.g., process facility 23), in real-time, at operating conditions, rather than standard conditions. According to an embodiment of the method, the method can include the steps of determining fluid pressure of the crude oil at a first location 55 (e.g., proximal or upper end portion along a vertically oriented extent 59) of the pipeline 21 carrying the crude oil flowing downward between the first location 55 and a second location 57 (e.g., distal or lower end portion along a vertically oriented extent 59) substantially vertically spaced apart from the first location 55 along the vertically oriented extent 59 and vertically below the first location 55 (block 121); and determining fluid pressure of the crude oil at the second location 57 along the vertically oriented extent 59 of the pipeline 21 (block 123). The method can also include the step of estimating API gravity at operating condition of the crude oil flowing through the vertically oriented extent 59 of the pipeline 21 (block 129), for example, either directly responsive to the determined fluid pressure at the first location 55, the determined fluid pressure at the second location 57, vertical elevation "h" between the sensors 51, 53, and approximate flow rate of the crude oil flowing through the vertically oriented extent 59 of the pipeline 21, or indirectly by first solving for the density (block 125) and specific gravity (block 127) of the crude oil flowing through the vertically oriented extent 59 of the pipeline. Further, the method and operations can alternatively include individually solving for density or specific gravity, particularly where API gravity is not required.

Figure 5:
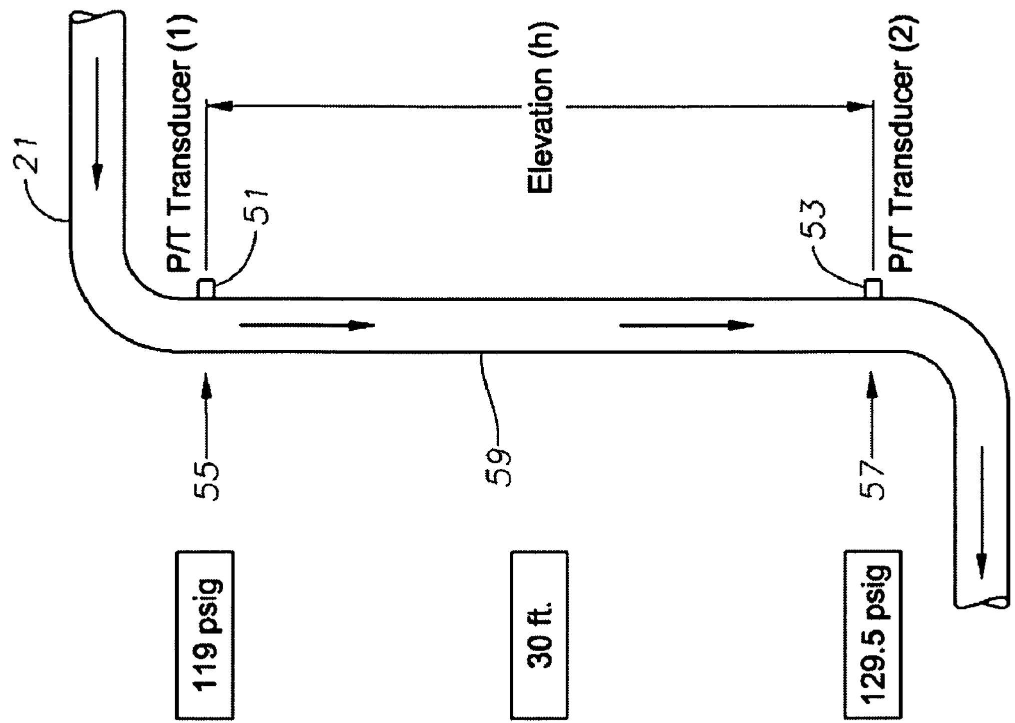
FIG. 5 is a schematic diagram of the portion of a pipeline including a pressure and temperature sensor assembly shown in FIG. 4 including exemplary values according to an embodiment of the present invention.

FIG. 5 provides an example of an implementation including exemplary numerical values according to the embodiment of the method illustrated in FIG. 7. According to the exemplary implementation, a flow stream of completely degassed crude oil is flowing in pipeline 21 with a known flow rate. In this example, the vertical distance between the two pressure sensors 51, 53, in the vertically oriented extent 59 is 30 feet; the upper sensor reading is 119 psig; and the lower sensor reading is 129.5 psig. Using these pressure readings, the following calculations can be utilized, for example, to determine density, specific gravity, and/or API gravity:

$$\begin{aligned} CrudeDensity(\rho_c) &= \frac{129.5 - 119}{30 * 12} + \text{correction factor (dynamic condition)} \\ &= 0.0291661\ \frac{\text{lb}}{\text{in}^3} + \text{correction factor (dynamic condition)} \end{aligned}$$

The "correction factor" for dynamic flow condition can be estimated, for example, from input table for known flow rates (approximate), or determined using empirical flow correlation (e.g., using a pipeline flow simulator). If for this example, the above the correction factor for the pressure drop due to friction was determined to be 0.5 psig then:

$$\begin{aligned} CrudeDensity(\rho_c) &= \frac{129.5 - 119}{30 * 12} + \frac{0.5}{30 * 12} \\ &= 0.030556\ \frac{\text{lb}}{\text{in}^3} * \frac{1728\ \text{in}^3}{\text{ft}^3} \\ &= 52.8\ \frac{\text{lb}}{\text{ft}^3} \end{aligned}$$

$$\text{Specific Gravity}(\gamma) = \frac{52.8}{62.4} = 0.8462$$

$$\text{Crude } API = \left[\frac{141.5}{0.8462} - 131.5\right] = 35.7^\circ\ API$$

This value for the crude API gravity can then readily be corrected for temperature between sensor locations, if desired.

Figure 8:
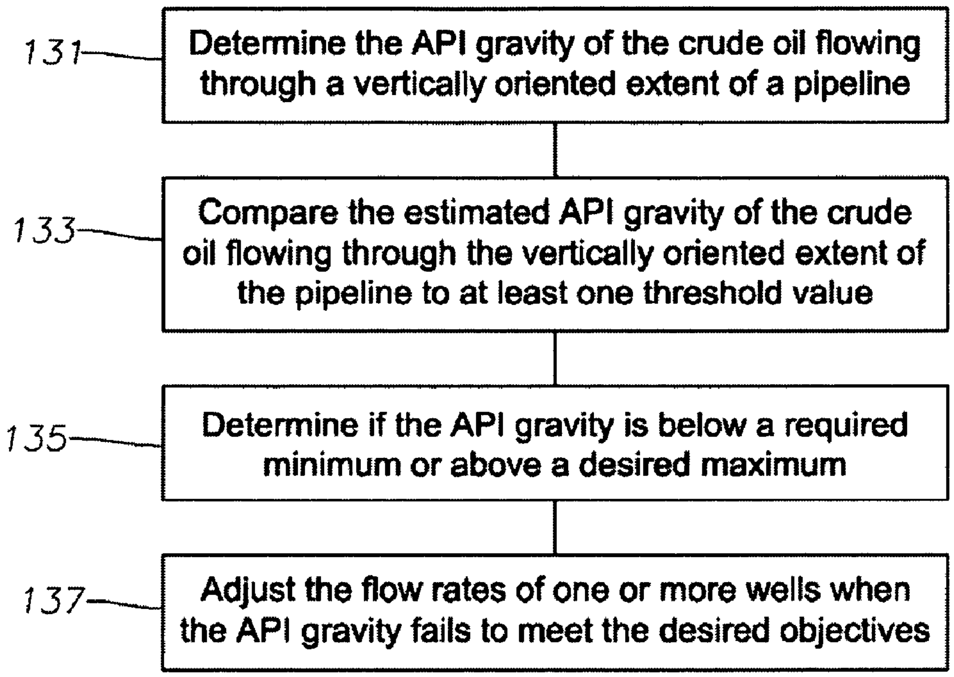
FIG. 8 is a schematic flow diagram of a method and operations for estimating and managing flowing fluid characteristics of a fluid flowing through a pipeline according to an embodiment of the present invention.

FIG. 8 provides a high-level flow diagram illustrating a method (and operations) for estimating and managing flowing fluid characteristics of a fluid stream (e.g., dehydrated and/or degassed crude oil) flowing through a pipeline (e.g., pipeline 21), for example, in a processing facility (e.g., process facility 23) in real-time, which includes application of the determined API gravity of the fluid stream to control the blend (grade) of the crude oil flowing through the pipeline 21. The method can include first determining the density, specific gravity, and/or API gravity, either under operating conditions or standard conditions. Specifically, according to an embodiment of the method, the crude oil includes a complex crude blend including a plurality of crude grades, for example, emanating from a plurality of oil wells (e.g., wells 25) in fluid communication with the processing facility 23 and controlled by a corresponding plurality of flow control valves (e.g., control valves 27). Accordingly, in a preferred embodiment of the method, the method can include determining the API gravity of the crude oil flowing through the vertically oriented extent 59 of the pipeline 21 (block 131), for example, using the process steps described previously; comparing the estimated API gravity of the complex blend of crude oil flowing through the vertically oriented extent 59 of the pipeline 21 to at least one threshold value (block 133) to determine if the API gravity has failed to meet the at least one threshold value (i.e., if it is below a required minimum or above a desired maximum) to thereby maintain the API gravity above a preselected desired minimum value or within a preselected desired range limit (block 135); and adjusting the flow rates of one or more of the plurality of wells 25 responsive to determining that the API gravity fails to meet the at least one threshold value (block 137) to thereby meet or maintain crude oil grade objectives.

Figure 9:
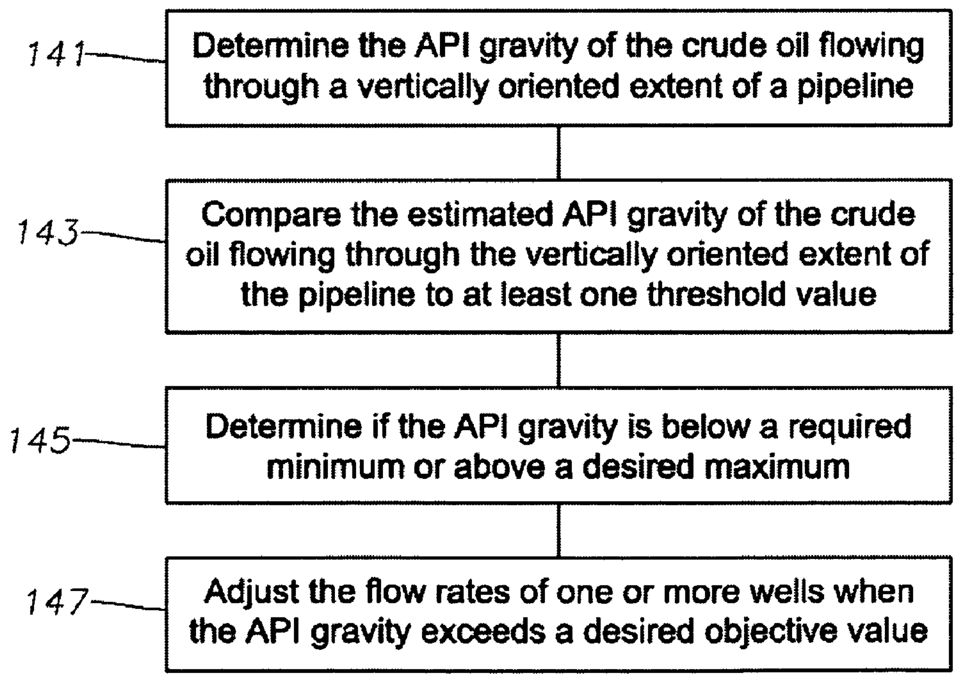
FIG. 9 is a schematic flow diagram of a method and operations for estimating and managing flowing fluid characteristics of a fluid flowing through a pipeline according to an embodiment of the present invention.

FIG. 9 provides a high-level flow diagram illustrating a method (and operations) for estimating and managing flowing fluid characteristics of a fluid stream (e.g., dehydrated and/or degassed crude oil) flowing through a pipeline (e.g., pipeline 21), for example, in a processing facility (e.g., process facility 23) in real-time, which includes application of the determined API gravity to control the blend (grade) of the crude oil flowing through the pipeline 21, according to another preferred configuration. According to such embodiment of a method, the method can include determining the API gravity of the crude oil flowing through the vertically oriented extent 59 of the pipeline 21 (block 141), for example, using the process steps described previously; comparing the estimated API gravity of the crude oil flowing through the vertically oriented extent 59 of the pipeline 21 to at least one threshold value (block 143) to determine if the API gravity has exceeded the at least one threshold value (i.e., if it is below a required minimum or above a desired maximum) to thereby maintain the API gravity within a preselected desired range limit (block 145); and when exceeding such threshold value or values, adjusting the flow rates of one or more of the wells 25 (block 147) to thereby meet or maintain crude oil grade objectives.

Notably, according to an exemplary implementation, production from a high-grade well 25 could be increased if the complex grade was determined to be insufficient, and production from a corresponding one or more wells 25 with a lower grade (typically a grade above or very close to the threshold), could be reduced a corresponding amount to maintain the overall flow rate of the crude oil flowing through pipeline 21. According to such implementation, production of a subpar well or wells 25 could be continued until such time that it is decided to rework or abandon the subpar well 25.

Figure 10:
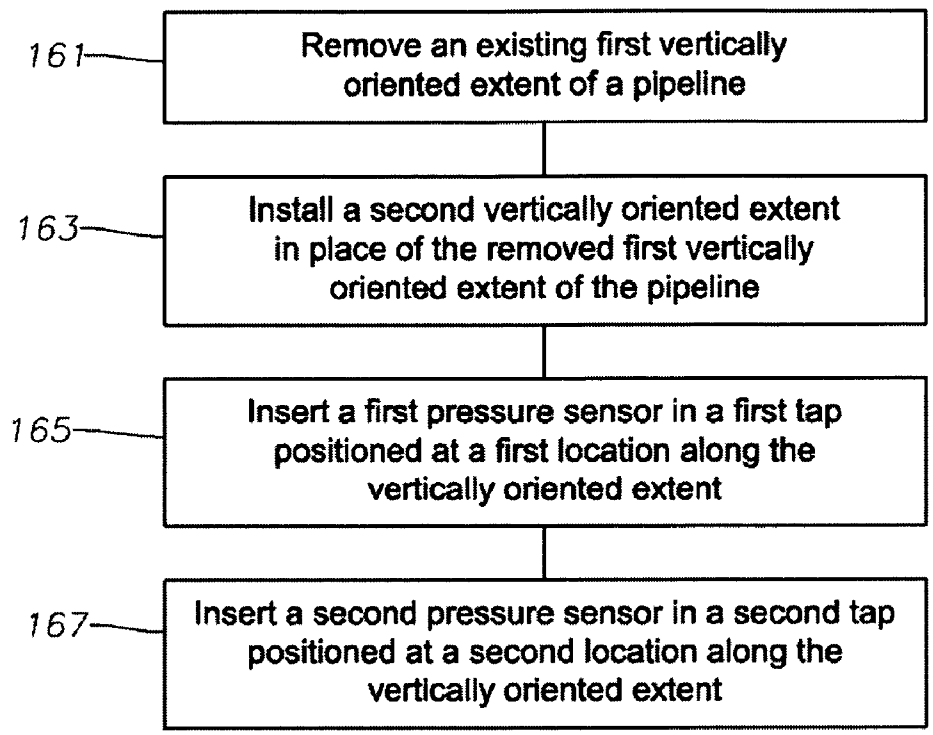
FIG. 10 is a schematic flow diagram of a method of retrofitting a portion of a pipeline according to an embodiment of the present invention.

FIG. 10 provides a high-level flow diagram illustrating preliminary steps regarding application of the sensors/sensor assemblies 51, 53, which can be utilized in order to implement the various embodiments of the methods and operations for estimating and managing flowing fluid characteristics of a fluid stream, as described above. According to an embodiment of such method, the method can include the steps of removing an existing first vertically oriented extent 59 of the pipeline 21 (block 161), and installing a second vertically oriented extent 59 in place of the removed first vertically oriented extent 59 of the pipeline 21 (block 163). The second vertically oriented extent 59 includes a pair of spaced apart apertures 61, 63, extending through the outer wall surface 69 of the pipeline 21 at the first and the second locations 55, 57, respectively, defining a pair of spaced apart pressure taps 61, 63. The method can also include inserting a first pressure sensor 51 in the first tap 61 positioned at the first location 55 (block 165), and inserting a second pressure sensor 53 in the second tap 63 positioned at the second location 57 (block 167).

Figure 11:
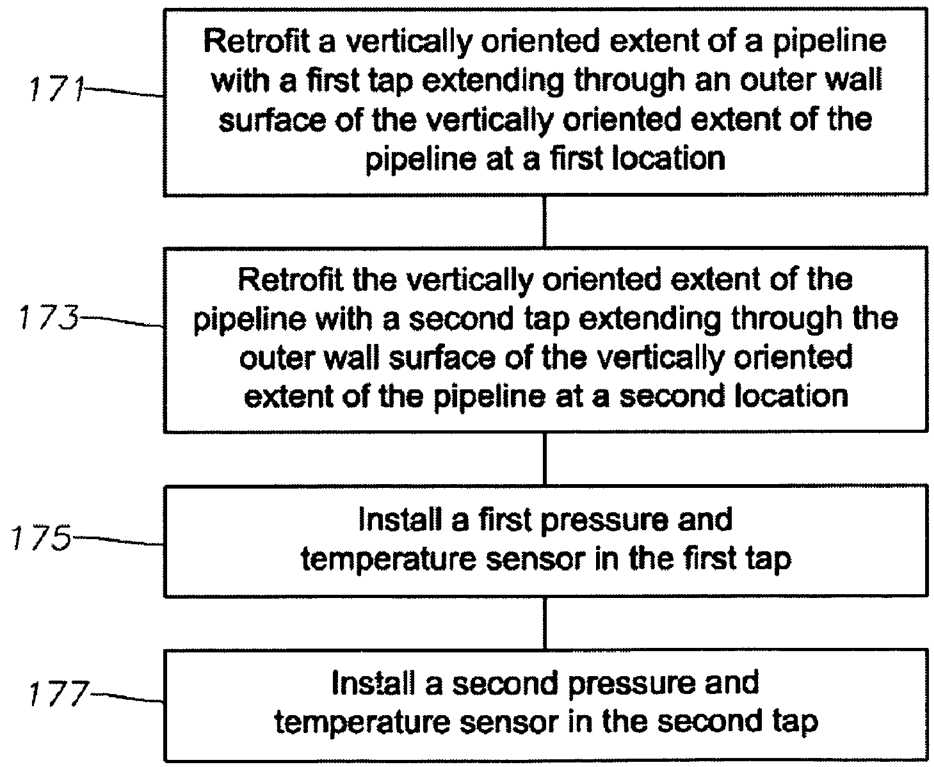
FIG. 11 is a schematic flow diagram of a method of retrofitting a portion of a pipeline according to an embodiment of the present invention.

FIG. 11 provides a high-level flow diagram illustrating preliminary steps regarding application of the sensors/sensor assemblies 51, 53, which can be utilized in order to implement the various embodiments of the methods and operations for estimating and managing flowing fluid characteristics of a fluid stream, as described above, according to another embodiment of the present invention. The method can include retrofitting a vertically oriented extent 59 of the pipeline 21 with a first aperture defining a first tap 61 extending through the outer wall surface 69 of the vertically oriented extent 59 of the pipeline 21 at the first location 55 (block 171), retrofitting the vertically oriented extent 59 of the pipeline 21 with a second aperture defining a second tap 63 extending through the outer wall surface 69 of the vertically oriented extent 59 of the pipeline 21 at the second location 57 (block 173), installing a first pressure and temperature sensor 51 in the first tap 61 (block 175), and installing a second pressure and temperature sensor 53 in the second tap 63 (block 177).

It is important to note that while the foregoing embodiments of the present invention have been described in the context of a fully functional system and process, those skilled in the art will appreciate that the mechanism of at least portions of the present invention and/or aspects thereof are capable of being distributed in the form of a computer readable medium storing a set of instructions in a variety of forms for execution on a processor, processors, or the like, and that embodiments of the present invention apply equally regardless of the particular type of signal bearing media used to actually carry out the distribution. Examples of computer readable media include, but are not limited to: nonvolatile, hard-coded type media such as read only memories (ROMs), CD-ROMs, and DVD-ROMs, or erasable, electrically programmable read only memories (EEPROMs), recordable type media such as floppy disks, hard disk drives, CD-R/RWs, DVD-RAMs, DVD-R/RWs, DVD+R/RWs, flash drives, and other newer types of memories, and transmission type media such as digital and analog communication links capable of storing the set of instructions. For example, such media can include both operating instructions and operations instructions described with respect to program product 71, the program product 71, itself, and the computer executable portions of the method steps according to the various embodiments of a method of estimating and managing flowing fluid characteristics of the fluid stream flowing through a pipeline, described above.

According to an embodiment of the computer readable medium and/or crude oil analysis and management program product 71 positioned thereon, such computer readable medium can include instructions that when executed by a processor, controller, or other form of computer (e.g., computer 31), cause the computer to perform the operations of receiving a signal/signals indicative of fluid pressure and temperature of the crude oil at a first location 55 from a sensor/sensor assembly 51 positioned along a proximal end portion of a vertically oriented extent 45 of the pipeline 21, receiving a signal/signals indicative of fluid pressure and temperature of the crude oil at a second location 57 from a sensor/sensor assembly 53 positioned along a distal end portion of the vertically oriented extent 45 of the pipeline 21, determining fluid pressure and temperature of the crude oil at the first location 55 responsive to the signal/signals provided by the first sensor/sensor assembly 51, and determining fluid pressure and temperature of the crude oil at the second location 57 responsive to the signal/signals provided by the second sensor/sensor assembly 53. The operations can also include estimating density, specific gravity, and/or API gravity of the crude oil flowing through the pipeline 21.

Particularly, the operations can include estimating density of the crude oil flowing through the vertically oriented extent 59 of the pipeline 21 responsive to the determined fluid pressure at the first location 55, the determined fluid pressure at the second location 57, and the vertical elevation "h" between a pressure sensor portion of the first sensor/sensor assembly 51 and a pressure sensing portion of the second sensor/sensor assembly 53; and where dynamic flow conditions exist, responsive to an approximate flow rate of the crude oil flowing downward through the vertically oriented extent 59 of the pipeline 21 (e.g., via a correction factor "CF"). Note, the correction factor for dynamic flow conditions can be estimated from an input table of known flow rates (not shown), or determined using empirical analysis/correlation (e.g., a pipeline flow simulator).

The operations can also include estimating specific gravity of the crude oil flowing through the vertically oriented extent 59 of the pipeline 21, for example, at standard conditions, responsive to: the estimated density of the crude oil, determined fluid temperature at the first location 55, and the determined fluid temperature at the second location 55, the density of water, and estimated thermal expansion (e.g., via a coefficient of isobaric thermal expansion); and/or estimating API gravity of the crude oil flowing through the vertically oriented extent 59 of the pipeline 21, for example, at standard conditions, responsive to the estimated specific gravity of the crude oil flowing through the vertically oriented extent 59 of the pipeline 21.

The operations can further include comparing the estimated API gravity of the crude oil flowing through the vertically oriented extent 59 of the pipeline 21 to at least one threshold value to determine if the API gravity has either failed to meet or exceeds the at least one threshold value to thereby maintain the API gravity above a preselected desired minimum value or within a preselected desired range limit, and adjusting the flow rate of one or more wells 25 responsive to determining that the API gravity fails to meet or exceeds the at least one threshold value (i.e., is below a required minimum or above a desired maximum).

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification. For example, although the description primarily focuses on crude oil, and more specifically, dehydrated degassed crude oil, one skilled in the art would recognize that embodiments of the present invention can be applied to any liquid fluid. Additionally, embodiments of the present invention can be applied to even static fluids trapped in the vertically oriented extent of the pipeline.

The invention claimed is:

1. A method for estimating and managing flowing fluid characteristics of a fluid stream of crude oil flowing through a processing facility pipeline in a processing facility in real-time, the method comprising the steps of:

measuring fluid pressure and temperature of dehydrated degassed crude oil at a first location along a vertically oriented extent of a processing facility pipeline carrying the dehydrated degassed crude oil flowing downward between the first location and a second location substantially vertically spaced apart from the first location along the vertically oriented extent and located vertically below the first location, the fluid pressure at the first location determined using a non-obstructive first pressure transducer coupled to a first fluid pressure tap extending through an outer wall surface of the vertically oriented extent of the pipeline;

measuring fluid pressure and temperature of the dehydrated degassed crude oil at the second location along the vertically oriented extent of the pipeline, the fluid pressure at the second location determined using a non-obstructive second pressure transducer coupled to a second fluid pressure tap extending through an outer wall surface of the vertically oriented extent of the pipeline, the first and the second pressure transducers positioned spaced apart along the vertically oriented extent of the pipeline at a predetermined vertical elevation of at least approximately 10 feet to enhance accuracy of measurements of a pressure differential between the first and the second locations, the pressure differential between the first and the second locations substantially provided by gravity acting upon the crude oil flowing downward through the vertically oriented extent, the fluid pressures measured at the first and the second locations along the vertically oriented extent of the processing facility pipeline carrying the crude oil flowing downward between the first location and the second location, to thereby negate a need for a separate fluid sampling line, a need for a fluid sampling pump, a need for a fluid collection extension inserted into the flow stream, and a need for a fluid flow having a vertically upward flow component between the first and the second locations;

the first and the second fluid pressure measurements being performed without use of a separate fluid sampling line, without use of a fluid sampling pump, without use of a fluid collection extension inserted into the flow stream, and without use of a vertically upward fluid flow between the first and the second locations, and the first and the second pressure measurements further being performed with at least insubstantial fluid flow disruption;

estimating specific gravity of the crude oil flowing through the vertically oriented extent of the pipeline responsive to: the determined fluid pressure at the first location, the determined fluid pressure at the second location, the vertical elevation between the first location and the second location, and approximate flow rate of the crude oil flowing through the vertically oriented extent of the pipeline; and estimating American Petroleum Institute (API) gravity of the crude oil flowing through the vertically oriented extent of the pipeline at standard condition responsive to: the estimated specific gravity of the crude oil flowing through the vertically oriented extent of the pipeline, the determined fluid temperature at the first location, and the determined fluid temperature at the second location.

2. A method as defined in claim 1, wherein the estimated API gravity is estimated according to the following calculations:

$$\rho_c = \frac{P_2 - P_1}{h} + CF;$$

$$\gamma = \frac{\rho_c}{\rho_w};$$

$$\gamma_{STD} = \gamma\left[1 - \beta\left(60°F - \left(\frac{T_1 + T_2}{2}\right)\right)\right];$$

$$\text{Crude } API_{STD} = \left(\frac{141.5}{\gamma_{STD}} - 131.5\right); \quad \text{and}$$

wherein:

$\rho_c$ is the density of the crude oil, $P_1$ is the fluid pressure at the first location, $P_2$ is the fluid pressure at the second location, h is the vertical elevation between the first and the second fluid pressure taps, CF is a correction factor that accounts for frictional pressure loss between the first and the second locations, $\gamma$ is the specific gravity of the crude oil at operating condition, $\rho_w$ is the density of water, $\gamma_{STD}$ is the specific gravity of the crude oil at standard condition, $\beta$ is the coefficient of isobaric thermal expansion, $T_1$ is the fluid temperature at the first location, and $T_2$ is the fluid temperature at the second location.

3. A method as defined in claim 2, wherein the vertically oriented extent of the pipeline is an existing fielded portion of the processing facility pipeline located at the processing facility;

wherein the flow rate of the crude oil flowing through the vertically oriented extent of the pipeline is a predetermined flow rate value based upon a determined value at an inlet portion of the pipeline located upstream of the first and the second pressure transducers, wherein the method further comprises the steps of:

determining the flow rate value at the inlet portion of the pipeline located upstream of the first and the second pressure transducers, and determining the correction factor responsive to the predetermined flow rate value and responsive to a calibration factor lookup table to thereby account for frictional pressure loss between the first and the second locations.

4. A method as defined in claim 2, wherein the vertically oriented extent of the pipeline is an existing fielded portion of the pipeline located at the processing facility;

wherein the flow rate of the crude oil flowing through the vertically oriented extent of the pipeline is a predetermined flow rate value based upon a determined value at an inlet portion of the pipeline located upstream of the first and the second pressure transducers; and wherein the method further comprises the steps of:

determining the flow rate value at the inlet portion of the pipeline located upstream of the first and the second pressure transducers, and determining the correction factor responsive to the predetermined flow rate value and responsive to a result of an empirical flow correlation to thereby account for frictional pressure loss between the first and the second locations.

5. A method as defined in claim 2, wherein the crude oil flowing through the vertically oriented extent of the pipeline comprises a mixture of a plurality of specific crude oil grades defining a complex crude oil blend received from the processing facility and provided to the processing facility by a plurality of oil wells each producing one of the plurality of crude oil grades, the method further comprising the steps of:

comparing the estimated API gravity of the crude oil flowing through the vertically oriented extent of the pipeline to at least one threshold value to determine if the API gravity has failed to meet the at least one threshold value; and adjusting the API gravity by adjusting a flow rate of one or more of the plurality of wells responsive to determining that the API gravity fails to meet the at least one threshold value to thereby maintain the API gravity above a preselected desired minimum value or within a preselected desired range limit.

6. A method as defined in claim 2, wherein the crude oil flowing through the vertically oriented extent of the pipeline comprises a mixture of a plurality of specific crude oil grades defining a complex crude oil blend received from the processing facility and provided to the processing facility by a plurality of oil wells each producing one of the plurality of crude oil grades, the method further comprising:

comparing the estimated API gravity of the crude oil flowing through the vertically oriented extent of the pipeline to at least one threshold value to determine if the API gravity has exceeded the at least one threshold value; and adjusting the API gravity by adjusting a flow rate of one or more of the plurality of wells responsive to determining that the API gravity exceeds the at least one threshold value to thereby maintain the API gravity within a preselected desired range limit.

7. A method as defined in claim 2, wherein the vertical elevation between the first and the second pressure taps is between approximately 20 feet and 100 feet to further enhance accuracy of measurements of the pressure differential.

8. A method as defined in claim 2, wherein the vertically oriented extent of the pipeline is a vertically oriented portion of a primary crude oil delivery pipeline of the processing facility having the downward flowing flowstream;

wherein the crude oil flowing through the vertically oriented extent of the pipeline is in fluid contact with at least portions of the first and the second pressure transducers; and wherein the method further comprises the step of:

positioning the first and the second pressure transducers along the vertically oriented extent of the pipeline having the downward flowing flowstream to thereby negate the need for a separate fluid sampling line, the need for a fluid sampling pump, the need for a fluid collection extension inserted into the flow stream, and the need for a fluid flow having a vertically upward flow component between the first and the second locations.

9. A method as defined in claim 1, wherein the vertically oriented extent of the pipeline is an existing fielded flowline associated with the processing facility, the method further comprising the step of:

retrofitting the vertically oriented extent of the pipeline with the first and the second pressure taps and the first and the second pressure transducers.

10. A method as defined in claim 1, wherein an outer surface wall of the vertically oriented extent of the pipeline associated with the first location and an outer surface wall of the vertically oriented extent of the pipeline associated with the second location each extend circumferentially around a common longitudinal axis.

11. A method for estimating and managing flowing fluid characteristics of a fluid stream of crude oil flowing through a processing facility pipeline in real-time, the method comprising the steps of:

measuring fluid pressure of dehydrated, degassed crude oil at a first location along a vertically oriented extent of a processing facility pipeline carrying the crude oil flowing downward between the first location and a second location substantially spaced apart from the first location along the vertically oriented extent and located vertically below the first location, the fluid pressure at the first location determined using a first pressure sensor at least partially extending through a first portion of an outer wall surface of the pipeline, the crude oil being dehydrated, degassed crude oil processed by the processing facility;

measuring fluid pressure at the second location along the vertically oriented extent of the pipeline, the fluid pressure at the second location determined using a second pressure sensor at least partially extending through a second portion of the outer wall surface of the pipeline, the first and the second pressure sensors positioned spaced apart along the vertically oriented extent of the pipeline at a predetermined vertical elevation of at least approximately 10 feet to enhance accuracy of measurements of a pressure differential between the first and the second locations, the pressure differential between the first and the second locations substantially provided by gravity acting upon the crude oil flowing downward through the vertically oriented extent, the fluid pressures measured at the first and the second locations along the vertically oriented extent of the processing facility pipeline carrying the crude oil flowing downward between the first location and the second location, to thereby negate a need for a separate fluid sampling line, a need for a fluid sampling pump, a need for a fluid collection extension inserted into the flow stream, and a need for a fluid flow having a vertically upward flow component between the first and the second locations, the first and the second fluid pressure measurements being performed without use of a separate fluid sampling line, without use of a fluid sampling pump, without use of a fluid collection extension inserted into the flow stream, and without use of a vertically upward fluid flow between the first and the second locations, and the first and the second pressure measurements further being performed with at least insubstantial fluid flow disruption; and estimating American Petroleum Institute (API) gravity of the crude oil flowing through the vertically oriented extent of the pipeline responsive to: the measured fluid pressure at the first location, the measured fluid pressure at the second location, the vertical elevation between the first location and the second location, fluid temperature at the first location, fluid temperature at the second location, and approximate flow rate of the crude oil flowing through the vertically oriented extent of the pipeline.

12. A method as defined in claim 11, further comprising the steps of:

measuring fluid temperature at the first location along the vertically oriented extent of the pipeline; and measuring fluid temperature at the second location along the vertically oriented extent of the pipeline;

wherein the first and the second temperature measurements are performed without use of a separate fluid sampling line, a fluid sampling pump, a fluid collection extension inserted into the flow stream, and without use of a vertically upward fluid flow between the first and the second locations, and are performed with an insubstantial or no fluid flow disruption; and wherein the step of estimating API gravity comprises the steps of:

estimating density of the crude oil flowing through the vertically oriented extent of the pipeline responsive to: the measured fluid pressure at the first location, the measured fluid pressure at the second location, the vertical elevation between the first location and the second location, and approximate flow rate of the crude oil flowing through the vertically oriented extent of the pipeline, estimating specific gravity of the crude oil flowing through the vertically oriented extent of the pipeline at standard condition responsive to: the estimated density, the measured fluid temperature at the first location, and the measured fluid temperature at the second location, and estimating API gravity of the crude oil flowing through the vertically oriented extent of the pipeline at standard condition responsive to the estimated specific gravity of the crude oil flowing through the vertically oriented extent of the pipeline.

13. A method as defined in claim 12, wherein the vertically oriented extent of the pipeline is a vertically oriented portion of a primary crude oil delivery pipeline vertically oriented at between approximately 40° to 90° to the horizon and having a downward flowing flowstream;

wherein the vertical elevation between the first and the second pressure sensors is between approximately 20 feet and 100 feet;

wherein the crude oil flowing through the vertically oriented extent of the pipeline is in fluid contact with at least portions of the first and the second pressure sensors; and wherein the method for the comprises the steps of:

positioning the first and the second pressure sensors along the vertically oriented extent of the pipeline having the downward flowing flowstream and 40° to 90° inclination, at the respective first and the second locations separated by the vertical elevation of between approximately 20 feet and 100 feet, to thereby the need for a separate fluid sampling line, the need for a fluid sampling pump, the need for a fluid collection extension inserted into the flow stream, and the need for a fluid flow having a vertically upward flow component between the first and the second locations, and extending each of the first and the second pressure sensors at least partially through the respective portion of the outer wall surface of the pipeline at a minimum extent necessary to sufficiently obtain pressure readings through continuous fluid contact with at least portions of the first and the second pressure sensors while minimizing any fluid flow disruption.

14. A method as defined in claim 13, wherein the flow rate of the crude oil flowing through the vertically oriented extent of the pipeline is a predetermined flow rate value based upon a determined value at an inlet portion of the pipeline located upstream of the first and the second pressure sensors, the method further comprising the steps of:

determining the flow rate value at the inlet portion of the pipeline located upstream of the first and the second pressure sensors; and determining a dynamic condition correction factor responsive to the predetermined flow rate value and responsive to a calibration factor lookup table to thereby account for frictional pressure loss between the first and the second locations.

15. A method as defined in claim 13, wherein the flow rate of the crude oil flowing through the vertically oriented extent of the pipeline is a predetermined flow rate value based upon a determined value at an inlet portion of the pipeline, the method further comprising the steps of:

determining the flow rate value at the inlet portion of the pipeline located upstream of the first and the second pressure sensors; and determining a dynamic condition correction factor responsive to the predetermined flow rate value and responsive to a result of an empirical flow correlation to thereby account for frictional pressure loss between the first and the second locations.

16. A method as defined in claim 13, wherein the estimated API gravity is determined according to the following calculations:

$$\rho_c = \frac{P_2 - P_1}{h} + CF;$$

$$\gamma = \frac{\rho_c}{\rho_w};$$

$$\gamma_{STD} = \gamma\left[1 - \beta\left(60°F - \left(\frac{T_1 + T_2}{2}\right)\right)\right];$$

$$\text{Crude } API_{STD} = \left(\frac{141.5}{\gamma_{STD}} - 131.5\right); \text{ and}$$

wherein:

$\rho_c$ is the density of the crude oil, $P_1$ is the measured fluid pressure at the first location, $P_2$ is the measured fluid pressure at the second location, h is the vertical elevation between the first and the second fluid pressure sensors, CF is a correction factor that accounts for frictional pressure loss between the first and the second locations, $\gamma$ is the specific gravity of the crude oil at operating condition, $\rho_w$ is the density of water, $\gamma_{STD}$ is the specific gravity of the crude oil at standard condition, $\beta$ is the coefficient of isobaric thermal expansion, $T_1$ is the measured fluid temperature at the first location, and $T_2$ is the measured fluid temperature at the second location.

17. A method as defined in claim 11, wherein the crude oil flowing through the vertically oriented extent of the pipeline comprises a mixture of a plurality of specific crude oil grades defining a complex crude oil blend received from the processing facility and provided to the processing facility by a plurality of oil wells each producing one of the plurality of crude oil grades, the method further comprising the steps of:

comparing the estimated API gravity of the crude oil flowing through the vertically oriented extent of the pipeline to at least one threshold value to determine if the API gravity has failed to meet the at least one threshold value; and adjusting the API gravity by adjusting a flow rate of one or more of the plurality of wells responsive to determining that the API gravity fails to meet the at least one threshold value to thereby maintain the API gravity above a preselected desired minimum value or within a preselected desired range limit.

18. A method as defined in claim 11, wherein the crude oil flowing through the vertically oriented extent of the pipeline comprises a mixture of a plurality of specific crude oil grades defining a complex crude oil blend received from the processing facility and provided to the processing facility by a plurality of oil wells each producing one of the plurality of crude oil grades, the method further comprising the steps of:

comparing the estimated API gravity of the crude oil flowing through the vertically oriented extent of the pipeline to at least one threshold value to determine if the API gravity has exceeded the at least one threshold value; and adjusting the API gravity by adjusting a flow rate of one or more of the plurality of wells responsive to determining that the API gravity exceeds the at least one threshold value to thereby maintain the API gravity within a preselected desired range limit.

19. A method is defined in claim 11, further comprising the steps of:

removing an existing first vertically oriented extent of the pipeline;

installing a second vertically oriented extent in place of the removed first vertically oriented extent of the pipeline, the second vertically oriented extent including a pair of spaced apart apertures extending through the outer wall surface of the pipeline at the first and the second locations, respectively, defining a pair of spaced apart pressure taps;

inserting the first pressure sensor in a first of the pair of spaced apart pressure taps positioned at the first location; and inserting the second pressure sensor in a second of the pair of spaced apart pressure taps positioned at the second location.

20. A method as defined in claim 11, wherein the first pressure sensor is a first pressure and temperature sensor, wherein the second pressure sensor is a second pressure and temperature sensor, the method further comprising the steps of:

retrofitting the vertically oriented extent of the pipeline with a first aperture defining a first tap extending through the outer wall surface of the vertically oriented extent of the pipeline at the first location;

retrofitting the vertically oriented extent of the pipeline with a second aperture defining a second tap extending through the outer wall surface of the vertically oriented extent of the pipeline at the second location;

installing the first pressure and temperature sensor in the first tap; and installing the second pressure and temperature sensor in the second tap.

21. A system to estimate and manage flowing fluid characteristics of a fluid stream of dehydrated, degassed crude oil flowing through a pipeline in a processing facility in real-time, the system comprising:

at least a portion of a pipeline for transporting dehydrated degassed crude oil including a vertically oriented extent substantially vertically oriented so that the crude oil flowing through the vertically oriented extent flows downward between a first location and a second location along the vertically oriented extent, the second location substantially vertically spaced apart from and vertically below the first location;

at least one first sensor connected to the at least a portion of the pipeline at the first location to provide at least one signal indicative of pressure and temperature of the crude oil at the first location;

at least one second sensor connected to the at least a portion of the pipeline at the second location to provide at least one signal indicative of pressure and temperature of the crude oil at the second location, the first and the second sensors having a preselected vertical elevation therebetween of at least approximately 10 feet to enhance accuracy of measurements of a pressure differential between the first and the second locations;

a controller to estimate and manage flowing fluid characteristics of the crude oil including a processor and memory coupled to the processor, the controller in communication with the at least one first sensor and the at least one second sensor; and crude oil analysis and management program product stored in the memory of the controller, the crude oil analysis and management program product including instructions that when executed by the processor of the controller, cause the controller to perform the operations of:

determining fluid pressure and temperature of the crude oil at the first location responsive to the at least one signal provided by the at least one first sensor, determining fluid pressure and temperature of the crude oil at the second location responsive to the at least one signal provided by the at least one second sensor, determining the pressure differential between the first and the second locations substantially provided by gravity acting upon the crude oil flowing downward through the vertically oriented extent, the fluid pressures and temperatures being sensed at the first and the second locations along the vertically oriented extent of the processing facility pipeline carrying the crude oil flowing downward between the first location and the second location to thereby negate a need for a separate fluid sampling line, a need for a fluid sampling pump, a need for a fluid collection extension inserted into the flow stream, and a need for a fluid flow having a vertically upward flow component between the first and the second locations, the first and the second fluid pressure and temperature determinations being performed without use of a separate fluid sampling line, without use of a fluid sampling pump, without use of a fluid collection extension inserted into the flow stream, and without use of a vertically upward fluid flow between the first and the second locations, and the first and the second pressure and temperature determinations being further performed with at least insubstantial fluid flow disruption;

estimating density of the crude oil flowing through the vertically oriented extent of the at least a portion of the pipeline responsive to: the determined fluid pressure at the first location, the determined fluid pressure at the second location, the vertical elevation between a pressure sensor portion of the at least one first sensor and a pressure sensing portion of the at least one second sensor, and approximate flow rate of the crude oil flowing downward through the vertically oriented extent of the at least a portion of the pipeline, estimating specific gravity of the crude oil flowing through the vertically oriented extent of the at least a portion of the pipeline at standard condition responsive to the estimated density of the crude oil, determined fluid temperature at the first location, and the determined fluid temperature at the second location, and estimating American Petroleum Institute (API) gravity of the crude oil flowing through the vertically oriented extent of the at least a portion of the pipeline at standard condition responsive to the estimated specific gravity of the crude oil flowing through the vertically oriented extent of the pipeline.

22. A system as defined in claim 21, wherein the system further comprises a plurality of flow control valves each in communication with the controller and each separately positioned to control a flow rate of crude oil entering the at least a portion of the pipeline received from the processing facility and provided to the processing facility by a plurality of oil wells;

wherein the crude oil comprises a complex crude blend including a plurality of crude grades provided by the plurality of oil wells; and wherein the operations further include:

comparing the estimated API gravity of the crude oil flowing through the vertically oriented extent of the at least a portion of the pipeline to at least one threshold value to determine if the API gravity has failed to meet the at least one threshold value to thereby maintain the API gravity above a preselected desired minimum value or within a preselected desired range limit, and adjusting the API gravity by adjusting the flow rate of one or more of the plurality of wells responsive to determining that the API gravity fails to meet the at least one threshold value.

23. A system as defined in claim 21, wherein the system further comprises a plurality of flow control valves each in communication with the controller and each separately positioned to control a flow rate of crude oil entering the at least a portion of the pipeline received from the processing facility and provided to the processing facility by a plurality of oil wells;

wherein the crude oil comprises a complex crude blend including a plurality of crude grades provided by the plurality of oil wells; and wherein the operations further include:

comparing the estimated API gravity of the crude oil flowing through the vertically oriented extent of the at least a portion of the pipeline to at least one threshold value to determine if the API gravity has exceeded the at least one threshold value to thereby maintain the API gravity within a preselected desired range limit, and adjusting the API gravity by adjusting the flow rate of one or more of the plurality of wells responsive to determining that the API gravity exceeds the at least one threshold value.

24. A system as defined in claim 21, wherein at least portions of the at least one first sensor extends through a first pressure tap in an outer wall surface of the at least portions of the pipeline at the first location, wherein at least portions of the at least one second sensor extends through a second pressure tap in the outer wall surface of the at least portions of the pipeline at the second location, wherein the crude oil flowing downward through the vertically oriented extent of the pipeline is in fluid contact with at least portions of the at least one first sensor and with at least portions of the at least one second sensor to minimize fluid flow disruption, and wherein the at least one first sensor and the at least one second sensor are positioned along the vertically oriented extent of the pipeline to thereby negate the need for a fluid collection extension inserted into the flow stream, the need for a separate fluid sampling line, the need for a fluid sampling pump, and the need for a fluid flow having a vertically upward flow component between the first and the second locations.

25. A system as defined in claim 21, wherein the flow rate of the crude oil flowing through the vertically oriented extent of the at least a portion of the pipeline is a predetermined flow rate value based upon a determined value at an inlet portion of the pipeline located upstream of the first and the second sensors; and wherein the operations further include:

determining the flow rate value at the inlet portion of the pipeline located upstream of the first and the second sensors, and determining a correction factor responsive to the predetermined flow rate value and responsive to a calibration factor lookup table to thereby account for frictional pressure loss between the first and the second locations.

26. A system as defined in claim 21, wherein the flow rate of the crude oil flowing through the vertically oriented extent of the at least a portion of the pipeline is a predetermined flow rate value based upon a determined value at an inlet portion of the pipeline located upstream of the first and the second sensors; and wherein the operations further include:

determining the flow rate value at the inlet portion of the pipeline located upstream of the first and the second sensors, and determining a correction factor responsive to the predetermined flow rate value and responsive to a result of an empirical flow correlation to thereby account for frictional pressure loss between the first and the second locations.

27. A system as defined in claim 21, wherein the at least one first sensor is a combined first pressure and temperature transducer, and wherein the at least one second sensor is a combined second pressure and temperature transducer.

28. Crude oil analysis and management program product stored in a tangible computer medium to estimate and manage flowing fluid characteristics of a fluid stream of dehydrated, degassed crude oil flowing through a pipeline in real-time, the program product including instructions that when executed by a computer, cause the computer to perform the operations of:

determining fluid pressure of crude oil at a first location along a vertically oriented extent of a pipeline carrying crude oil flowing downward between the first location and a second location substantially spaced apart from the first location along the vertically oriented extent and vertically below the first location, responsive to at least one signal provided by at least one first sensor associated with the first location, the crude oil being dehydrated, degassed crude oil;

determining fluid pressure of the crude oil at the second location responsive to at least one signal provided by at least one second sensor associated with the second location and positioned spaced apart from the first sensor to provide a vertical elevation therebetween of at least approximately 10 feet to enhance accuracy of measurements of a pressure differential between the first and the second locations, the pressure differential between the first and the second locations substantially provided by gravity acting upon the crude oil flowing downward through the vertically oriented extent, the fluid pressures being sensed at the first and the second locations along the vertically oriented extent of the processing facility pipeline carrying the crude oil flowing downward between the first location and the second location to thereby negate a need for a separate fluid sampling line, a need for a fluid sampling pump, a need for a fluid collection extension inserted into the flow stream, and a need for a fluid flow having a vertically upward flow component between the first and the second locations, the first and the second pressure determinations being performed without use of a separate fluid sampling line, without use of a fluid sampling pump, without use of a fluid collection extension inserted into the flow stream, without use of a vertically upward fluid flow between the first and the second locations, and the first and the second pressure determinations further being performed with at least insubstantial fluid flow disruption; and estimating American Petroleum Institute (API) gravity of the crude oil flowing through the vertically oriented extent of the pipeline responsive to: the determined fluid pressure at the first location, the determined fluid pressure at the second location, vertical elevation between the at least one first sensor and the at least one second sensor, fluid temperature at the first location, fluid temperature at the second location, and approximate flow rate of the crude oil flowing through the vertically oriented extent of the pipeline.

29. Program product as defined in claim 28, wherein the operations further comprise:

estimating density of the crude oil flowing through the vertically oriented extent of the pipeline;

determining fluid temperature of the crude oil at the first location responsive to the at least one signal provided by the at least one first sensor;

determining fluid temperature of the crude oil at the second location responsive to the at least one signal provided by the at least one second sensor, the first and the second temperature determinations being performed without use of a separate fluid sampling line, a fluid sampling pump, without use of a fluid collection extension inserted into the flow stream, and without use of a vertically upward fluid flow between the first and the second locations, and being performed with an insubstantial or no fluid flow disruption; and estimating specific gravity of the crude oil flowing through the vertically oriented extent of the pipeline at standard condition responsive to: the estimated density of the crude oil, determined fluid temperature at the first location, and the determined fluid temperature at the second location to thereby estimate the API gravity of the crude oil, and wherein the estimated API gravity of the crude oil is at standard condition.

30. Program product as defined in claim 28, wherein the crude oil comprises a complex crude blend including a plurality of crude grades received from a processing facility and provided to the processing facility by a plurality of oil wells; and wherein the operations further comprise:

comparing the estimated API gravity of the crude oil flowing through the vertically oriented extent of the pipeline to at least one threshold value to determine if the API gravity has failed to meet the at least one threshold value to thereby maintain the API gravity above a preselected desired minimum value or within a preselected desired range limit, and adjusting the API gravity by providing an adjustment signal to adjust a flow rate of one or more of a plurality of wells each having at least one flow control valve each separately positioned to control a flow rate of crude oil entering the pipeline received from a corresponding separate one of the plurality of oil wells, responsive to determining that the API gravity failed to meet the at least one threshold value.

31. Program product as defined in claim 28, wherein the crude oil comprises a complex crude blend including a plurality of crude grades received from a processing facility and provided to the processing facility by a plurality of oil wells; and wherein the operations further comprise:

comparing the estimated API gravity of the crude oil flowing through the vertically oriented extent of the pipeline to at least one threshold value to determine if the API gravity has exceeded the at least one threshold value to thereby maintain the API gravity within a preselected desired range limit, and adjusting the API gravity by providing an adjustment signal to adjust a flow rate of one or more of the plurality of wells responsive to determining that the API gravity exceeds the at least one threshold value.

32. Program product as defined in claim 28, wherein the flow rate of the crude oil flowing through the vertically oriented extent of the pipeline is a predetermined flow rate value based upon a determined value at an inlet portion of the pipeline located upstream of the first and the second sensors; and wherein the operations further comprise:

determining the flow rate value at the inlet portion of the pipeline (21) located upstream of the first and the second sensors, and determining a correction factor responsive to the predetermined flow rate value and responsive to a calibration factor lookup table to thereby account for frictional pressure loss between the first and the second locations.

33. Program product as defined in claim 28, wherein the flow rate of the crude oil flowing through the vertically oriented extent of the pipeline is a predetermined flow rate value based upon a determined value at an inlet portion of the pipeline; and wherein the operations further include determining a correction factor responsive to the predetermined flow rate value and responsive to a result of an empirical correlation to thereby account for frictional pressure loss between the first and the second locations.

34. Program product as defined in claim 28, wherein the estimated API gravity is determined according to the following calculations:

$$\rho_c = \frac{P_2 - P_1}{h} + CF;$$

$$\gamma = \frac{\rho_c}{\rho_w};$$

$$\gamma_{STD} = \gamma\left[1 - \beta\left(60°F - \left(\frac{T_1 + T_2}{2}\right)\right)\right];$$

$$\text{Crude } API_{STD} = \left(\frac{141.5}{\gamma_{STD}} - 131.5\right); \text{ and}$$

wherein:

$\rho_c$ is the density of the crude oil, $P_1$ is the fluid pressure at the first location, $P_2$ is the fluid pressure at the second location, h is the vertical elevation between the at least one first pressure sensor and the at least one second pressure sensor, CF is a correction factor that accounts for frictional pressure loss between the first and the second locations, $\gamma$ is the specific gravity of the crude oil at operating condition, $\rho_w$ is the density of water, $\gamma_{STD}$ is the specific gravity of the crude oil at standard condition, $\beta$ is the coefficient of isobaric thermal expansion, $T_1$ is the fluid temperature at the first location, and $T_2$ is the fluid temperature at the second location.

* * * * *